US008232255B2

(12) United States Patent (10) Patent No.: US 8,232,255 B2
Hoffman et al. (45) Date of Patent: Jul. 31, 2012

(54) METHODS FOR VACCINATING AGAINST MALARIA

(75) Inventors: Stephen L. Hoffman, Gaithersburg, MD (US); Ruobing Wang, Potomac, MD (US); Judith E. Epstein, Kensington, MD (US); Joseph D. Cohen, Brussels (BE)

(73) Assignees: GlaxoSmithKline Biologicals S.A., Rixensart (BE); The United States of America as represented by the Secretary of the Navy, Washington, DC (US)

( * ) Notice: Subject to any disclaimer, the term of this patent is extended or adjusted under 35 U.S.C. 154(b) by 648 days.

(21) Appl. No.: 10/532,081

(22) PCT Filed: Oct. 22, 2003

(86) PCT No.: PCT/US03/33462
§ 371 (c)(1),
(2), (4) Date: Mar. 27, 2006

(87) PCT Pub. No.: WO2004/037189
PCT Pub. Date: May 6, 2004

(65) Prior Publication Data
US 2006/0188527 A1 Aug. 24, 2006

Related U.S. Application Data

(60) Provisional application No. 60/420,265, filed on Oct. 23, 2002, provisional application No. 60/447,026, filed on Feb. 13, 2003.

(51) Int. Cl.
*A61K 39/00* (2006.01)
*A61K 48/00* (2006.01)

(52) U.S. Cl. .................. 514/44 R; 424/184.1
(58) Field of Classification Search .......... 514/44; 424/184.1
See application file for complete search history.

(56) References Cited

U.S. PATENT DOCUMENTS

| 5,928,902 A | 7/1999 | De Wilde et al. | |
|---|---|---|---|
| 2005/0208078 A1* | 9/2005 | Hoffman et al. | 424/272.1 |
| 2005/0266017 A1* | 12/2005 | Druilhe et al. | 424/191.1 |

OTHER PUBLICATIONS

Aguiar et al., "Enhancement of the Immune Response in Rabbits to a Malaria DNA Vaccine by Immunization with a Needle-free Jet Device" *Vaccine* 20:275-80 (2001).
Aidoo et al., "Identification of Conserved Antigenic Components for a Cytotoxic T Lymphocyte-inducing Vaccine Against Malaria" *Lancet* 345:1003-07 (1995).
Al-Yaman et al., "Relationship Between Humoral Response to *Plasmodium falciparum* Merozoite Surface Antigen-2 and Malaria Morbidity in a Highly Endemic Area of Papua New Guinea" *Am. J. Trop. Med. Hyg.* 51:593-602 (1994).
Al-Yaman et al., "Assessment of the Role of the Humoral Response to *Plasmodium falciparum* MSP2 Compared to RESA and SPf66 in protecting Papua New Guinean Children from Clinical Malaria" *Parsite Immunol.* 17:493-501 (1995).
Anders et al., "Immunisation with Recombinant AMA-1 Protects Mice Against Infection with *Plasmodium chabaudi*" *Vaccine* 16(2-3):240-47 (1998).
Barouch et al., "Control of Viremia and Prevention of Clinical AIDS in Rhesus Monkeys by Cytokine-augmented DNA Vaccination" *Science* 290:486-92 (2000).
Blackman et al., A Single Fragment of a Malaria Merozoite Surface Protein Remains on the Parasite During Red Cell Invasion and is the Target of Invasion-inhibiting Antibodies. *J. Exp. Med.* 172:379-82 (1990).
Brazolot Millan et al., "CpG DNA Can Induce Strong Th1 Humoral and Cell-mediated Immune Responses Against Hepatitis B Surface Antigen in Young Mice" *PNAS-USA* 95:15553-58 (1998).
Burns et al., "The 3' portion of the Gene for a *Plasmodium yoelii* Merozoite Surface Antigen Encodes the Epitope Recognized by a Protective Monoclonal Antibody" *PNAS-USA* 5:602-06 (1988).
Calarota et al., "Cellular Cytotoxic Response Induced by DNA Vaccination in HIV-1-Infected Patients" *Lancet* 351:1320-25 (1998).
Chang et al., "A Recombinant Baculovirus 42-kilodalton C-terminal Fragment of *Plasmodium falciparum* Merozoite Surface Protein 1 Protects *Aotus* Monkeys Against Malaria" *Infect. Immun.* 64:253-61 (1996).
Charoenvit et al., "Characterization of *Plasmodium yoelii* Monoclonal Antibodies Directed Against Stage-specific Sporozoite Antigens" *Infect. Immun.* 55:604-08 (1987).
Charoenvit et al., "Inability of Malaria Vaccine to Induce Antibodies to a Protective Epitope within its Sequence" *Science* 251:668-71 (1991).
Charoenvit et al., "*Plasmodium yoelii*: 17-kD Hepatic and Erythrocytic Stage Protein is the Target of an Inhibitory Monoclonal Antibody" *Exp. Parasitol.* 80:419-29 (1995).
Charoenvit et al., "CD4+ T-cell- and Gamma Interferon Dependent Protection Against Murine Malaria by Immunization with Linear Synthetic Peptide from *Plasmodium yoelii* 17-kilodaldon Hepatocyte Erythrocyte Protein" *Infect. Immun.* 67:5604-14 (1999).
Clark et al., "46-53 kD Glycoprotein from the Surface of *Plasmodium falciparum* Merozoites" *Mol. Biochem .* 32:15-24 (1989).
Collins et al., "Selection of Different Strains of *Plasmodium falciparum* for Testing Blood-stage Vaccines in *Aotus nancymai* Monkeys" *Am. J. Trop. Med. Hyg.* 51:224-32 (1994).
Collins et al., "Protective Immunity Induced in Squirrel Monkeys with Recombinant Apical Membrane Antigen-1 of *Plasmodium fragile*" *Am. J. Trop. Med. Hyg.* 51:711-19 (1994).
Daly et al., "A Recombinant 15-kilodalton Carboxyl-terminal Fragment of *Plasmodium yoelii* 17XL Merozoite Surface Protein 1 Induces a Protective Immune Response in Mice" *Infect. Immun.* 61:2462-67 (1993).

(Continued)

*Primary Examiner* — Albert Navarro
(74) *Attorney, Agent, or Firm* — Finnegan, Henderson, Farabow, Garrett & Dunner, LLP

(57) ABSTRACT

The invention pertains to methods for protecting against malaria infection by vaccination. The method of the invention involves priming an anti-malaria immune response with a DNA-based vaccine and boosting that response with a protein-based vaccine. The method of the invention also relates to broadening the resulting immune response by boosting with a protein-based vaccine.

17 Claims, 6 Drawing Sheets

OTHER PUBLICATIONS

Dame et al., "Structure of the Gene Encoding the Immunodominant Surface Antigen on the Sporozoite of the Human Malaria Parasite *Plasmodium falciparum*" *Science* 225:593-99 (1984).

Daubersies et al., "Protection Against *Plasmodium falciparum* Malaria in Chimpanzees by Immunization with the Conserved Pre-erythrocytic Liver-stage Antigen 3" *Nat. Med.* 6:1258-63 (2000).

Davis et al., "CpG DNA is a Potent Enhancer of Specific Immunity in Mice Immunized with Recombinant Hepatitis B Surface Antigen" *J. Immunol.* 160:870-76 (1998).

Deans, "Protective Antigens of Bloodstage *Plasmodium knowlesi* Parasites" *Philos. Trans. R. Soc. Lond. Biol.* 307:159-69 (1984).

Deans et al., "Vaccination Trials in Rhesus Monkeys with a Minor, Invariant, *Plasmodium knowlesi* 66 kD Merozoite Antigen" *Parasite Immunol.* 10:535-52 (1988).

Delplace et al., "Protein p126: a Parasitophorous Vacuole Antigen Associated with the Release of *Plasmodium falciparum* Merozoites" *Biol. Cell* 64:215-21 (1988).

Doolan et al., "Circumventing Genetic Restriction of Protection Against Malaria with Multi-gene DNA Immunization: CD8+ T cell, Interferon-gamma, and Nitric Oxide Dependent Immunity" *J. Exp. Med.* 183:1739-46 (1996).

Doolan et al., "Identification and Characterization of the Protective Hepatocyte Erythrocyte Protein 17 kDa Gene of *Plasmodium yoelii*, Homolog of *Plasmodium falciparum* Exported Protein 1" *J. Biol. Chem.* 271:17861-68 (1996).

Doolan et al., "Degenerate Cytotoxic T Cell Epitopes from *P. falciparum* Restricted by HLA-A and HLA-B Supertypes Alleles" *Immunity* 7:97-112 (1997).

Doolan et al., "DNA Vaccination as an Approach to Malaria Control: Current Status and Strategies" *Curr. Topic Microbiol. Immunol.* 226:37-56 (1998).

Doolan et al., "IL-12 and NK Cells are Required for Antigen-specific Adaptive Immunity Against Malaria Initiated by CD8+ T Cells in the *Plasmodium yoelii* Model" *J. Immunol.* 163:884-92 (1999).

Egan et al., "Efficacy of Murine Malaria Sporozoite Vaccines: Implications for Human Vaccine Development" *Science* 236:453-56 (1987).

Epstein et al., "Safety, Tolerability and Lack of Antibody Responses Following Administration of a *Pf*CSP DNA Malaria Vaccine via Needle or Needle-free Jet Injection, and Comparison of Intramuscular and Combination Intramuscular/Intradermal Routes" *Human Gene Therapy* 13:1551-60 (2002).

Etlinger et al., "Ability of Recombinant or Native Proteins to Protect Monkeys Against Heterologous Challenge with *Plasmodium falciparium*" *Infect. Immun.* 59:3498-503 (1991).

Freeman et al., "Characteristics of the Protective Response of BALB/c Mice Immunized with a Purified *Plasmodium yoelii* Schizont Antigen" *Clin. Exp. Immunol.* 54:609-16 (1983).

Gordon et al., "Safety, Immunogenicity, and Efficacy of a Recombinantly Produced *Plasmodium falciparum* Circumsporozoite Protein-hepatitis B Surface Antigen Subunit Vaccine" *J. Infect. Dis.* 171:1576-85 (1995).

Gramzinski et al., "Malaria DNA Vaccines in *Aotus* Monkeys" *Vaccine* 15:913-15 (1997).

Gurunathan et al., "DNA Vaccines: a Key for Inducing Long-term Cellular Immunity" *Curr. Opin. Immunol.* 12:442-47 (2000).

Harnyuttanakorn et al., "Inhibitory Monoclonal Antibodies Recognise Epitopes Adjacent to a Proteolytic Cleavage Site on the RAP-1 Protein of *Plasmodium falciparum*" *Mol. Biochem. Parasitol.* 55:177-86 (1992).

Hedstrom et al., "In Vitro Expression and In Vivo Immunogenicity of *Plasmodium falciparum* Pre-erythrocytic Stage DNA Vaccines" *Int. J. Molec. Med.* 2:29-38 (1998).

Herrington et al., "Successful Immunization of Humans with Irradiated Sporozoites: Humoral and Cellular Responses of the Protected Individuals" *Am. J. Trop. Med. Hyg.* 45:539-47 (1991).

Hilgers et al., "Synergistic Effects of Synthetic Adjuvants on the Humoral Immune Response" *Int. Arch. Allergy Appl. Immunol.* 79:392-96 (1986).

Hilgers et al., "Synthetic Sulpholipopolysaccharides: Novel Adjuvants for Humoral Immuneresponses" *Immunology* 60:141-46 (1987).

Hill et al., "Molecular Analysis of the Association of HLA-B53 and Resistance to Severe Malaria" *Nature* 360:434-39 (1992).

Hoffman et al., "Malaria Vaccines-Targeting Infected Hepatocytes" *Nat. Med.* 6:1218-19 (2000).

Holder et al., "Immunization Against Blood-stage Rodent Malaria Using Purified Parasite Antigens" *Nature* 294:361-64 (1981).

Horn et al., "Cancer Gene Therapy Using Plasmid DNA: Purification of DNA for Human Clinical Trials" *Human Gene Therapy* 6:565-73 (1995).

Inselburg et al., "Protective Immunity Induced in *Aotus* Monkeys by Recombinant SERA Proteins of *Plasmodium falciparum*" *Infect. Immun.* 59:1247-50 (1991).

Inselburg et al., "Protective Immunity Induced in *Aotus* Monkeys by a Recombinant SERA Protein of *Plasmodium falciparum*: Adjuvant Effects on Induction of Protective Immunity" *Infect. Immun.* 61:2041-47 (1993).

Kedzierski et al., "Immunization with Recombinant *Plasmodium yoelii* Merozoite Surface Protein 4/5 Protects Mice Against Lethal Challenge" *Infect. Immun.* 68:6034-37 (2000).

Kensil et al., "Separation and Characterization of Saponins with Adjuvant Activity from Quillajasaponaria Molina Cortex" *J. Immunol.* 146:431-37 (1991).

Kensil, "Saponins as Vaccine Adjuvants" *Crit. Rev. Ther. Drug Carrier Syst.* 12:1-55 (1996).

Kester et al., "Efficacy of Recombinant Circumsporozoite Protein Vaccine Regimens Against Experimental *Plasmodium falciparum* Malaria" *J. Infect. Dis.* 183:640-47 (2001).

Khusmith et al., "Protection Against Malaria by Vaccination with Sporozoite Surface Protein 2 Plus CS Protein" *Science* 252:715-18 (1991).

Khusmith et al., "Complete Protection Against *Plasmodium yoelii* by Adoptive Transfer of a CD8+ Cytotoxic T Cell Clone Recognizing Sporozoite Surface Protein 2" *Infect. Immun.* 62:2979-83 (1994).

Krieg et al., "CpG Motifs in Bacterial DNA Trigger Direct B-cell Activation" *Nature* 374:546-49 (1995).

Kumar et al., "Immunogenicity and In Vivo Efficacy of Recombinant *Plasmodium falciparum* Merozoite Surface Protein-1 in *Aotus* Monkeys" *Mol. Med.* 1:325-32 (1995).

Kumar et al., "Immunogenicity and Efficacy in *Aotus* Monkeys of Four Recombinant *Plasmodium falciparum* Vaccines in Multiple Adjuvant Formulations Based on the 19-Kilodalton C Terminus of Merozoite Surface Protein 1" *Infect. Immun.* 68:2215-23 (2000).

Lacaille-Dubois et al., "A Review of the Biological and Pharmacological Activities of Saponins" *Phytomedicine* 2:363-86 (1996).

Le et al., "Safety, Tolerability, and Humoral Immune Responses after Intramuscular Administration of a Malaria DNA Vaccine to Healthy Adult Volunteers" *Vaccine* 18:1893-901(2000).

Lee et al., "Quantification of the Number of Cytotoxic T Cells Specific for an Immunodominant HCV-specific CTL Epitope Primed by DNA Immunization" *Vaccine* 18:1962-68 (2000).

Luke et al., "An ospA-based DNA Vaccine Protects Mice Against Infection with *Borrelia burgdorferi*" *J. Inf. Dis.* 175:91-97 (1997).

Majarian et al., "Passive Immunization Against Murine Malaria with an IgG3 Monocloncal Antibody" *J. Immunol.* 132: 3131-37 (1984).

Malik et al., "Human Cytotoxic T Lymphocytes Against the *Plasmodium falciparum* Circumsporozoite Protein" *PNAS-USA* 88:3300-04 (1991).

Martin et al., "Plasmid DNA Malaria Vaccine: The Potential for Genomic Integration Following Intramuscular Injection" *Human Gen. Ther.* 10:759-68 (1999).

McCluskie et al., "CpG DNA is a Potent Enhancer of Systemic and Mucosal Immune Responses Against Hepatitis B Surface Antigen with Intranasal Administration to Mice" *J. Immunol.* 161:4463-66 (1998).

Moreno et al., "Cytotoxic CD4+ T Cells from a Sporozoite-immunized Volunteer Recognize the *Plasmodium falciparum* CS Protein" *Int. Immunol.* 3:997-1003 (1991).

Mosmann et al., "TH1 and TH2 Cells: Different Patterns of Lymphokine Secretion Lead to Different Functional Properties" *Ann. Rev. Immunol.* 7:145-73 (1989).

Musti et al., "Transcriptional Mapping of Two Yeast Genes Coding for Glyceraldehyde 3-phosphate Dehydrogenase Isolated by Sequence Homology with the Chicken Gene" *Gene* 25:133-43 (1983).

Oeuvray et al., "Merozoite Surface Protein-3:A Malaria Protein Inducing Antibodies that Promote *Plasmodium falciparum* Killing by Cooperation with Blood Monocytes" *Blood* 84:1594-602 (1994).

Oeuvray et al., "A Novel Merozoite Surface Antigen of *Plasmodium falciparum* (MSP-3), Identified by Cellular-antibody Cooperative Mechanism Antigenicity and Biological Activity of Antibodies" *Mem. Inst. Oswaldo Cruz.* 89(Supp 2):77-80 (1994).

Panina-Bordignon et al., "Universally Immunogenic T Cell Epitopes: Promiscuous Binding to Human MHC class II and Promiscuous Recognition by T cells" *Eur. J. Immunol.* 12:2237-42 (1989).

Parker et al., "Plasmid DNA Malaria Vaccine: Tissue Distribution and Safety Studies in Mice and Rabbits" *Human Gene Ther.* 10:741-58 (1999).

Perrin et al., "Characterization of Antigens from Erythrocytic Stages of *Plasmodium falciparum* Reacting with Human Immune Sera" *Trans. R. Soc. Trop. Med. Hyg.* 75:163-65 (1981).

Perrin et al., "Inhibition of *P. falciparum* Growth in Human Erythrocytes by Monoclonal Antibodies" *Nature* 289:301-03 (1981).

Potocnjak et al., "Monovalent Fragments (Fab) of Monoclonal Antibodies to a Sporozoite Surface Antigen (Pb44) Protect Mice Against Malaria Infection" *J. Exp. Med.* 151:1504-13 (1980).

Ramasamy, "Studies on Glycoproteins in the Human Malaria Parasite *Plasmodium falciparum*-lectin Binding Properties and the Possible Carbohydrate-protein Linkage" *Immunol. Cell Biol.* 65:147-52 (1987).

Ramasamy et al., "Characterization of an Inhibitory Monocloncal Antibody Defined Epitope on a Malaria Vaccine Candidate Antigen" *Immunol. Lett* 23:305-09 (1990).

Rattan et al., "Protein Synthesis: Post-translational Modifications and Aging" *Ann. NY Acad. Sci.* 663:48-62 (1992).

Ridley et al., "A Rhoptry Antigen of *Plasmodium falciparum* is Protective in Saimiri Monkeys" *Parasitology* 101:187-92 (1990).

Rodrigues et al., "CD8+ Cytolytic T Cell Clones Derived Against the *Plasmodium yoelii* Circumsporozoite Protein Protect Against Malaria" *Int. Immunol.* 3:579-85 (1991).

Rogers et al., "Multistage Multiantigen Heterologous Prime Boost Vaccine for *Plasmodium knowlesi* Malaria Provides Partial Protection in Rhesus Macaques" *Infect. Immun.* 69:5565-72 (2001).

Romero et al., "Cloned Cytotoxic T Cells Recognize an Epitope in the Circumsporozoite Protein and Protect Against Malaria" *Nature* 341:323-25 (1989).

Saul et al., "Protective Immunization with Invariant Peptides of the *Plasmodium falciparum* Antigen MSA2" *J. Immunol.* 148:208-11 (1992).

Schofield et al., "A Rhoptry Antigen of *Plasmodium falciparum* Contains Conserved and Variable Epitopes Recognised by Inhibitory Monoclonal Antibodies" *Mol. Biochem. Parasitol.* 18:183-95 (1986).

Schofield et al., "Gamma-interferon, CD8+ T cells and Antibodies Required for Immunity to Malaria Sporozoites" *Nature* 330:664-66 (1987).

Sedegah et al., "Improving Protective Immunity Induced by DNA-based Immunization: Priming with Antigen and GM-CSF-encoding Plasmid DNA and Boosting with Antigen-expressing Recombinant Poxvirus" *J. Immunol.* 164:5905-12 (2000).

Seder et al., "Vaccines Against Intracellular Infections Requiring Cellular Immunity" *Nature* 406:793-98 (2000).

Seguin et al., "Induction of Nitric Oxide Synthase Protects Against Malaria in Mice Exposed to Irradiated *Plasmodium berghei* Infected Mosquitoes: Involvement of Interferon Gamma and CD8+ T Cells" *J. Exp. Med.* 180:353-58 (1994).

Seifter et al., "Analysis for Protein Modifications and Nonprotein Cofactors" *Meth. Enzymol.* 182:626-46 (1990).

Shi et al., "Natural Immune Response to the C-terminal 19-kilodalton Domain of *Plasmodium falciparum* Merozoite Surface Protein 1" *Infect. Immun.* 64:2716-23 (1996).

Siddiqui et al., "Merozoite Surface Coat Precursor Protein Completely Protects *Aotus* Monkeys Against *Plasmodium falciparum* Malaria" *PNAS-USA* 84:3014-18 (1987).

Sim et al., "Primary Structure of the 175K *Plasmodium falciparum* Erythrocyte Binding Antigen and Identification of a Peptide which Elicits Antibodies that Inhibit Malaria Merozoite Invasion" *J. Cell Biol.* 111:1877-84 (1990).

Sim et al., "*Plasmodium falcipaum:* Further Characterization of a Functionally Active Region of the Merozoite Ligand EBA-175" *Exp. Parasitol.* 78:259-68 (1994).

Stoute et al., "A Preliminary Evaluation of a Recombinant Circumsporozoite Protein Vaccine Against *Plasmodium falciparum* Malaria" *N. Eng. J. Med.* 336:86-91(1997).

Stoute et al., "Long-term Efficacy and Immune Responses Following Immunization with the RTS,S Malaria Vaccine" *J. Infect. Dis.* 178:1139-44 (1998).

Thomas et al., "High Prevalence of Natural Antibodies Against *Plasmodium falciparum* 83-kilodalton Apical Membrane Antigen (PF83/AMA-1) as Detected by Capture-enzyme-linked Immunosorbent Assay Using Full-length Baculovirus Recombinant PF83/AMA-1" *Am. J. Trop. Med. Hyg.* 51:730-40 (1994).

Thomas et al., "Aspects of Immunity for the AMA-1 Family of Molecules in Humans and Non-human Primates Malarias" *Mem. Inst. Oswaldo Cruz.* 89(Suppl 2):67-70 (1994).

Valenzuela et al., "Nucleotide Sequences of the Gene Coding for the Major Protein of Hepatitis B Virus Surface Antigen" *Nature* 280:815-19 (1979).

Wang et al., "Protection Against Malaria by *Plasmodium yoelii* Sporozoite Surface Protein 2 Linear Peptide Induction of CD4+ T Cell- and IFN-gamma-dependent Elimination of Infected Hepatocytes" *J. Immunol.* 157:4061-67 (1996).

Wang et al., "Induction of Antigen-specific Cytotoxic T Lymphocytes in Humans by a Malaria DNA Vaccine" *Science* 282:476-80 (1998).

Wang et al., "Simultaneous Induction of Multiple Antigen-specific Cytotoxic T Lymphocytes in Nonhuman Primates by Immunization with a Mixture of Four *Plasmodium falciparum* DNA Plasmids" *Infect. Immun.* 66:4193-202 (1998).

Weiss et al., "CD8+ T Cells (cytotoxic/suppressors) are Required for Protection in Mice Immunized with Malaria Sporozoites" *PNAS-USA* 85:573-76 (1988).

Weiss et al., "A T Cell Clone Directed at the Circumsporozoite Protein which Protects Mice Against Both *Plasmodium yoelii* and *Plasmodium berghei*" *J. Immunol.* 149:2103-09 (1992).

WHO Report. "State of the World's Vaccines and Immunization." Geneva: World Health Organization, pp. 124-131 (1996).

Wizel et al., "Induction of Murine Cytotoxic T Lymphocytes Against *Plasmodium falciparum* Sporozoite Surface Protein 2" *Eur. J. Immunol.* 24:1487-95 (1994).

Wizel et al., "HLA-A2-restricted Cytotoxic T Lymphocyte Responses to Multiple *Plasmodium falciparum* Sporozoite Surface Protein 2 Epitopes in Sporozoite-immunized Volunteers" *J. Immunol.* 155:766-75 (1995).

Wold, "Post-translational Protein Modifications: Perspectives and Prospects" in Post-translational Covalent Modification of Proteins (B. C. Johnson, ed. Academic Press, New York, 1983) pp. 1-12.

Yang et al., "Partial Protection Against *Plasmodium vivax* Blood-stage Infection in Saimiri Monkeys by Immunization with a Recombinant C-terminal Fragment of Merozoite Surface Protein 1 in Block Copolymer Adjuvant" *Infect. Imm.* 67:342-49 (1999).

Zinsser Microbiology (Wolfgang K. Joklik, Hilda P. Willett, D. Bernard Amos, and Catherine M. Wilfert eds., 20th ed, Appleton and Lange 1992) pp. 1180-1183.

Bojang et al., "Efficacy of RTS, S/AS02 Malaria Vaccine Against *Plasmodium falciparum* Infection in Semi-immune Adult Men in The Gambia: A Randomised Trial" *Lancet* 358:1927-34 (2001).

Epstein et al., "Safety, Tolerability, and Antibody Responses in Humans After Sequential Immunization with PfCSP DNA Vaccine Followed by the Recombinant Protein Vaccine RTS,S/AS02A" *Vaccine* 22:1592-603 (2004).

Hoffman et al., "Can Malaria DNA Vaccines on Their Own be as Immunogenic and Protective as Prime-Boost Approaches to Immunization?" *Developments in Biologicals* 104:121-32 (2000).

Jones et al., "Protection of *Aotus* Monkeys by *Plasmodium falciparum* EBA-175 Region II DNA Prime-Protein Boost Immunization Regimen" *J. Infec. Dis.* 183:303-12 (2001).

Lalvani et al., "Potent Induction of Focused Th-1-Type Cellular and Humoral Immune Responses by RTS,S/SBAS2, a Recombinant *Plasmodium falciparum* Malaria Vaccine" *J. Infec. Dis.* 180:1656-64 (1999).

Search Report dated Sep. 2, 2004 from PCT application PCT/US03/3346.

Supplemental Search Report dated Mar. 13, 2006 from EPO Application 03779163.9 ( PCT/US03/3346).

Wang et al., "Induction in Humans of $CD8^+$ and $CD4^+$ T Cell and Antibody Responses by Sequential Immunization with Malaria DNA and Recombinant Protein" *J. Immunol.* 172:5561-69 (2004).

Wang, R. et al., Induction of $CD4^+$ T Cell-Dependent $CD8^+$ Type 1 Responses in Humans by a Malaria DNA Vaccine, PNAS., vol. 98, No. 19, pp. 10817-10822, (Sep. 11, 2001).

Doolan, D. L. et al., "DNA-Based Vaccines Against Malaria: Status and Promise of the Multi-Stage Malaria DNA Vaccine Operation", International Journal for Parasitology, vol. 31, pp. 753-762, (2001).

* cited by examiner

Fig. 1a : PfCSP-specific CTLs after DNA immunization

Fig. 1b : PfCSP-specific CTLs Just Before RTS,S Boost

Fig. 1c: PfCSP-specific CTLs after RTS,S boost

METHODS FOR VACCINATING AGAINST MALARIA

CROSS REFERENCE TO RELATED APPLICATIONS

This application is based on and claims the benefit of U.S. Provisional Application Ser. No. 60/420,265, filed Oct. 23, 2002 and U.S. Provisional Application Ser. No. 60/447,026, filed Feb. 13, 2003. The entire disclosure of these provisional applications is relied upon and incorporated by reference herein.

INTRODUCTION

Malaria is one of the greatest public health problems in the tropics and subtropics. Each year, 300 to 500 million people contract new plasmodium infections, and up to 2.7 million die from malaria in the developing world (10). *Plasmodium falciparum* is the plasmodium species responsible for the majority of deaths due to malaria.

The life cycle of *P. falciparum* occurs in four separate stages, three of which occur in the human body. See 115 generally. In the first stage, a mosquito carrying infectious sporozoites in its salivary glands obtains a blood meal from a person and, in doing so, transmits these sporozoites to the person's bloodstream. Once in the parenchymal cells of the liver, sporozoites replicate to form merozoites. In the second stage, the merozoites travel throughout the bloodstream, infecting red blood cells (RBCs). Once the RBC is full of merozoites, it bursts, releasing progeny that infect new RBCs. Anemia is a common symptom as this stage of infection. Eventually, some of these RBCs will also produce male and female gametocytes (the third stage). In the final stage, an uninfected mosquito feeds on an infected person, ingesting the gametocytes. In the mosquito, fertilization of the female gametocyte eventually leads to the production of infectious sporozoites, thus completing the cycle.

When a pathogen such as *P. falciparum* enters the human body, the body responds by activating the immune system. At first, a generalized response occurs followed by a pathogen-specific response. The pathogen-specific response targets antigens unique to the invading pathogen. The two major arms of the pathogen-specific response are cellular and humoral. $CD8^+$ and $CD4^+$ T cells participate in the cellular immune response. Specifically, $CD8^+$ T cells produce cytokines such as interferon gamma (IFN-$\gamma$), which has a variety of stimulatory effects on other components of the immune system such as macrophages. A special class of $CD8^+$ T cells, cytotoxic T lymphocytes (CTLs), specifically kill infected cells that express pathogen antigens on their surface. In contrast, $CD4^+$ T cells or T helper cells promote the development of CTLs and induce B cells to divide and ultimately produce antibodies. T helper cells may be divided into two subsets, $T_H1$ and $T_H2$ $CD4^+$ T cells, which are identified according to the profile of cytokines they produce. The second arm of the pathogen-specific immune response consists of the humoral response, in which B cells replicate, differentiate, and eventually produce antibodies which bind directly to pathogens. Antibodies are particularly useful for coating a pathogen not associated with any host cell. Phagocytic cells, such as macrophages, then engulf antibody coated pathogens.

In the context of a malarial infection, different arms of the pathogen-specific immune response are most effective at particular stages of the *P. falciparum* life cycle. When infectious sporozoites travel to the liver and enter liver cells, the sporozoites become intracellular pathogens, spending little time outside the infected cells. At this stage, $CD8^+$ T cells and $CD4^+$ T cells are especially important because these T cells and their cytokine products, such as IFN-$\gamma$, are primarily responsible for the killing of infected host cells. Substantial data from the Naval Medical Research Center (NMRC) Malaria Program and other laboratories indicate that eliminating the intracellular liver parasites in murine malaria is dependent upon CD8+ T cell responses directed against peptides expressed by liver stage parasites (45). Depletion of CD8+ T cells abrogates protection against sporozoite challenge (27, 31, 90, 93, 108) and adoptive transfer of CD8+ T cells to naïve animals confers protection (56, 85, 87, 109).

DNA vaccines induce cell-mediated immune responses, including the antigen-specific $CD8^+$ cytotoxic T lymphocytes (CTLs) and Th1 biased $CD4^+$ T cell responses that are the major mechanisms of protection against intracellular pathogens and tumors (6, 11, 45, 63, 104, 106). However, thus far DNA vaccines have proved suboptimal for induction of protective immune responses in humans.

In contrast, when a malarial infection reaches the second stage and infects RBCs, infectious merozoites not only replicate inside RBCs, they circulate freely in the bloodstream. Antibodies are most effective at dealing with this stage of infection for two reasons. First, CTLs require infected host cells to present antigens on a special protein called MHC-I. RBCs do not express MHC-L thereby reducing the effectiveness of CTLs. Second, as discussed above, antibodies mediate phagocytosis of pathogens not associated with host cells. Thus, in the second stage of infection, both B cells and $CD4^+$ T cells, which stimulate B cells, are important for combating the infection.

The complexity of the human immune response to *P. falciparum*, as well as a multi-stage parasite life cycle with stage-specific expression of proteins, contribute to the difficulty in developing a vaccine against *P. falciparum*. Nonetheless, the need for a malaria vaccine remains.

The sporozoite stage of *P. falciparum* has been identified as a potential target of a malaria vaccine. The major surface protein of the sporozoite is known as circumsporozoite protein (CS protein). A protein from strain 7G8 has been cloned, expressed and sequenced (21). It is characterized by having a central immunodominant repeat region comprising a tetrapeptide Asn-Ala-Asn-Pro repeated 37 times but interspersed with four minor repeats Asn-Val-Asp-Pro. In other strains, the number of major and minor repeats vary as well as their relative position. This central portion is flanked by an N and C terminal portion composed of non-repetitive amino acid sequences designated as the repeatless portion of the CS protein.

A DNA-based vaccine containing a plasmid that expresses the *P. falciparum* circumsporozoite (PfCSP) gene was developed by Vical, Inc. San Diego, Calif. and the Naval Medical Research Center (47). The vaccine was composed of naked DNA in phosphate buffered saline (PBS) at a concentration of 2500 µg per 1 ml. The plasmid contained the full-length gene encoding the entire PfCSP gene, with expression controlled by the promoter/enhancer of the CMV IE gene, the 5' untranslated region of the CMV IE gene, and the transcriptional terminator of the bovine growth hormone gene (64). To enhance expression and secretion of the antigen in mammalian cells, the sequence encoding the leader peptide from human tissue plasminogen activator protein (hTPA) was added to the 5' end of the coding sequence. Thus, the two open reading frame sequences contained in the PfCSP plasmid encode the kanamycin resistance protein and the hTPA leader/PfCSP fusion protein (40). The PfCSP plasmid contains no known viral or oncogenic protein coding sequences.

The plasmid contains 6261 nucleotide base pairs and has a molecular weight of $4.07 \times 10^6$ gmu, assuming that the average base pair of DNA is 650 gmu.

The PfCSP DNA plasmid was constructed by using segments of cloned DNA which were obtained from purified plasmids utilizing standard molecular genetic techniques. The plasmid was produced in bacterial (*E. coli*) cell culture with a kanamycin selection medium. After fermentation of bacterial cells, plasmid DNA was purified.

Preclinical immunogenicity studies of the PfCSP DNA vaccine were conducted at the NMRC prior to the start of clinical trials. Specifically, the PfCSP plasmid was transiently transfected into cultured mammalian cells after which antigen expression was evaluated by immunoblot analysis. This plasmid was also tested for its capacity to induce antigen-specific antibody and CTL responses in mice and nonhuman primates (40, 105). Studies in the mouse model demonstrated induction of antigen-specific CTL and antibody responses following immunization with plasmid DNA (30). Studies further established that the intramuscular (IM route of immunization was optimal for induction of CD8+ Th1 immune responses, as reported in other systems (30). In addition, subsequent studies showed that all six Rhesus monkeys immunized via the IM route with the PfCSP plasmid, either alone or in combination with up to four other plasmids encoding other pre-erythrocytic liver stage *P. falciparum* proteins, had detectable antigen-specific CTL and/or antibody responses (106).

Before use in clinical trials, extensive preclinical safety studies were conducted. These studies included 1) a mouse tissue distribution study of plasmid DNA administered either via the intravenously (IV) route or the IM route; 2) repeat-dose safety studies in mice and rabbits; and 3) plasmid DNA integration studies in mice (67, 75). These studies are summarized below.

Plasmid distribution studies: Parker et al. assessed plasmid distribution in different tissues of mice (75). Mice received a single dose of the PfCSP plasmid, which was 25 times the highest mg/kg dose recommended for humans, either IV or IM. Tissues were harvested and PCR was used to assess the presence of plasmid DNA at the following time points: 1 hour, 2 days and 4-weeks post-administration after administration IV and 2 days, 4 weeks, and 8 weeks after administration IM. Plasmid DNA was found distributed throughout all tissues one hour after IM administration. By 2 days after IM administration, plasmid was found only in bone marrow, blood, and at the injection site, with highest levels at the injection site. Plasmid DNA was detected only at the injection site by 1 week after IM administration. After IV administration, the PfCSP DNA plasmid was found distributed in low levels to all tissues except the gonads and brain. Four weeks after IV administration, DNA plasmid was detected only in the lung of one animal.

Repeat dose safety studies: Parker et al. also addressed the safety of giving repeated doses of the vaccine in mice and rabbits (75). In a repeat-dose safety study in mice, animals received 8 repeated IM injections of the PfCSP DNA plasmid over a 28-day period at doses of 1.0 µg, 10 µg, and 100 µg (cumulative doses equivalent to 5-500 times the proposed human dose on a mg/kg basis). There was no evidence of abnormal hematology or serum chemistry, abnormal histopathology, or induction of antinuclear antibodies or antibodies to dsDNA. In a repeat-dose safety study in rabbits, animals received six weekly IM injections of the plasmid at doses of 150 µg and 450 µg. Again, as in the murine studies, there was no evidence of abnormal hematology or serum chemistry, abnormal histopathology, or induction of antinuclear antibodies or antibodies to dsDNA. Thus, Parker's studies showed that the PfCSP plasmid distributes well throughout the host's tissues, that the plasmid was retained in some of those tissues for extended periods, and that the plasmid is safe for use in man, as shown by the lack of adverse reaction when it is administered to a volunteer.

Integration studies: Martin et al. assessed whether the PfCSP plasmid integrates into the host chromosomal DNA (67). A single dose of plasmid DNA was injected into each mouse and tissues were analyzed 30 and 60 days after administration by PCR analysis to a sensitivity of 1-10 copies per microgram of DNA. Overall, these studies provided no evidence for plasmid integration and suggested that if there is any integration of plasmid DNA into genomic DNA, it is at an extremely low level, several thousand times lower than that expected from spontaneous mutation.

Once investigators verified the safety of the PfCSP vaccine, the NMRC conducted two Phase-I clinical trials. In the first trial, healthy malaria-naïve adult volunteers received the PfCSP DNA vaccine between 1997 and 1998 (33, 62, 105, 106). A total of 20 volunteers were enrolled and 5 volunteers were assigned to each of four dosage groups: 20 µg, 100 µg, 500 µg, and 2500 µg with 3 doses given at one month intervals. As described by Le et al., all of the doses were well tolerated with no episodes of severe or serious adverse events (62). There were four moderate adverse events; all were considered unlikely to be related to the vaccine administration. The most common complaint was pain and tenderness at the injection site. This was mild, lasting less than 48 hours, and required no medication. No volunteers had any significant serum biochemical abnormalities.

None of the 20 subjects had the induction of anti-dsDNA antibodies or an increase in ANA (anti-nuclear antibody) titer from baseline. Wang et al. showed that none of the volunteers developed antibodies to PfCSP as assessed by indirect fluorescent antibody test (FAT) against air-dried sporozoites and enzyme linked immunosorbent assay (ELISA) against recombinant and synthetic peptides. However, 11 of the 20 volunteers had antigen-specific, genetically restricted CTL activity. Specifically, the CTL responses were CD8+ T cell dependent, peptide-specific and genetically HLA-restricted since there was little or no recognition of autologous targets that were incubated with a control peptide or of HLA class I-mismatched targets that were incubated with the specific peptide. In addition, the DNA-induced CTLs were genetically restricted by multiple HLA alleles (105, 107). CTL positivity was dose-related. In the remaining 9 volunteers, CTLs were not detected in any assays conducted after each of the immunizations.

In the second clinical trial, initiated in April 1999, 14 healthy adult volunteers were immunized at 0, 4 and 8 weeks with the PfCSP DNA vaccine by three different routes: conventional needle IM (intramuscular), Biojector® IM, and Biojector® IM (70% of dose) plus ID (intradermal) (30% of dose). The Biojector® is a needleless jet injection device. Given the small size of the study, the HLA diversity of the volunteers was restricted to the most common HLA class I sub-type in this population, HLA A2, to permit intergroup comparisons of the genetically-restricted CTL response. Ten of the volunteers who participated in this study subsequently participated in an additional trial which employed the methods of the invention. This trial and its outcome are further described in the "Examples" section below.

Overall, the vaccine was safe and well-tolerated. Volunteers did not experience any severe or serious adverse events (AEs) that were vaccine related. None of the volunteers experienced significant laboratory abnormalities associated with administration of the PfCSP vaccine by any of the three routes tested (33).

Regarding immune responses to the vaccine, none of the volunteers developed antibodies to the PfCSP as assessed by IFAT against air-dried sporozoites and ELISA against recombinant and synthetic peptides (107). The absence of PfCSP-specific antibodies was somewhat surprising because both the Biojector jet injection device and the ID route of immunization have been associated with improved antibody production in animal models (1, 37, 62). T cell responses were measured by IFN-γ in ELISPOT assays. In performing these assays, peptides including T cell epitopes of the CSP protein encoded by the PfCSP plasmid were used.

All four volunteers in the needle IM group responded to 7/9 peptides in 17.6% (26/148) of assays. All five volunteers in the Biojector IM group responded to 9/9 peptides in 26.5% (49/185) of assays. Four out of five volunteers in the Biojector IM/ID group responded to 7/9 peptides in 17.3% (32/185) of assays. Eight of the 14 volunteers had detectable CTL responses. Of those eight, two were in the needle IM group (responding to 4/7 peptides in a total of 5/126 assays), three were in the Biojector IM group (responding to 6/8 peptides in a total of 11/168 assays), and three were in the Biojector IM/ID group (responding to 6/6 peptides in at total of 14/162 assays) (107). Overall, this trial established that Biojector IM route of inoculation was the most effective for inducing an antigen-specific IFN-γ response and that Biojector IM or IM/ID route was most effective at inducing antigen-specific CTL responses.

In sum, these two clinical trials demonstrate that the PfCSP polynucleotide vaccine can elicit an antigen-specific, genetically restricted CD8+ T cell response as measured by peptide-specific, genetically restricted, CD8+ T cell dependent CTL activity and by IFN-γ production (105, 107). Volunteers from the second clinical trial, when tested one year after the administration of the last dose of the PfCSP polynucleotide vaccine, failed to demonstrate any CD8+ antigen-specific T cell responses as measured above.

As discussed above, in addition to CD8+ T cell responses, antibodies against any peptide of the PfCSP protein also play an important role in controlling malarial infections (1, 78, 99). Although most recipients of the PfCSP DNA vaccine developed CD8+ antigen-specific T cell responses, none developed any anti-CSP specific antibodies. In contrast, investigators have shown that RTS,S can elicit robust antibody responses to CSP (53, 99, 100). RTS,S is also a potent inducer of TH-1 type cellular and humoral immunity with RTS,S-specific CD4+ T cell responses predominantly focused on the Th2R immunodominant polymorphic region (61).

Administration of 2 or 3 doses of RTS,S has protected a mean of 44% of more than 60 volunteers challenged with *P. falciparum* 2-3 weeks after last immunization (8, 54, 99), and protected 70% of semi-immune Gambians for 2 months after last immunization (8). However, this protection is of short duration (8, 100). Immunization with RTS,S induces anti-PfCSP antibodies and $CD4^+$ T cell-dependent IFN-γ responses, but no $CD8^+$ T cell-dependent CTL or IFN-γ responses have been detected (61).

THE INVENTION

The instant invention provides a new vaccine method that primes an immune response with a priming vaccine comprising a polynucleotide encoding at least one first malarial antigen and then boosts the primed response with a boosting vaccine comprising at least one polypeptide comprising at least one second malarial antigen having at least one epitope in common with the at least one first malaria antigen of the priming vaccine. This combination provides three significant improvements to current anti-malaria vaccination strategies.

First, the combination of two heterologous vaccines activates both arms of the immune system, CD8+ T cells, CD4+ T cells, and antibodies. Specifically, based on the results of clinical trials using the PfCSP vaccine or the RTS,S vaccine, neither vaccine alone established a sustainable immune response that invoked CD8+ T cells, CD4+ T cells, and antibodies to CSP. The instant invention improves this outcome by combining the two vaccines, thereby eliciting all three types of responses. Specifically, the PfCSP vaccine primes a CD8+ T cell response and the RTS,S vaccine boosts that T cell response. As the RTS,S vaccine also elicits anti-CSP antibodies and CD4+ T cells, the resulting immune response to CSP includes both the CD8+ and CD4+ T cell responses and antibody responses. We refer to this overall strategy of vaccination, priming with one vaccine and then boosting with a different vaccine that shares at least one common epitope with the priming vaccine, as a "prime/boost" strategy.

The invention's second significant improvement over current vaccination strategies lies in the fact that it employs a protein vaccine to stimulate a CD8+ T cell response in humans. The method of the invention boosts T cell responses by using a protein-based vaccine that was heretofore considered ineffective at stimulating CD8+ T cell responses (61).

Finally, the third significant improvement over current anti-malaria vaccination strategies provided by the invention is that it broadens the immune response in two ways. First, a broader repertoire of IFN-γ-producing T cells (Tc1 and Th1) was induced by DNA priming/RTS,S boost, since priming with DNA initiated both CD4+ T cell-dependent CD8+ type 1 (Tc1) and CD4+ type 1 (Th1) IFN-γ responses, whereas RTS,S alone induced only CD4+ T cell-dependent Th1 IFN-γ responses. Second, when administered alone, the PfCSP vaccine primes a certain population of CD8+ T cells. Likewise, the RTS,S vaccine alone primes a certain population of CD4+ T cells and B cells that make a certain set of antibodies. When combined, however, the resulting CD8+ T cell response not only covers the epitopes initially primed by the PfCSP vaccine, the response also covers additional epitopes not initially identified after the priming PfCSP vaccination. The concept that a protein vaccine would boost an established CD8+ T cell response, as well as broaden it, is unexpected in light of what was known in the art about protein vaccines.

BRIEF DESCRIPTION OF THE INVENTION

The instant invention pertains to methods for immunizing a human against malaria comprising the steps of: a) priming an immune response in a human by administration of a priming vaccine comprising a polynucleotide encoding at least one malaria antigen; and b) boosting the primed immune response by subsequent administration of a boosting vaccine comprising at least one polypeptide which comprises at least one malaria antigen having at least one epitope in common with the malaria antigen or antigens of the priming vaccine to invoke both a cellular immune response and a humoral immune response against malaria.

In one embodiment of the invention, the priming vaccine encodes the same polypeptide present in the boosting vaccine. In other embodiments, either the priming vaccine encodes part of the malaria antigen present in the boosting vaccine or the polypeptide present in the boosting vaccine is a portion of the malaria antigen encoded by the priming vaccine. In another embodiment, the vaccines share at least one malarial T cell epitope. In yet another embodiment, the vaccines share at least one malarial CD8+ T cell epitope. In an alternate embodiment, the two vaccines share several malarial epitopes.

Any pathogen that causes malaria may be used in the method of the invention. In one embodiment, the pathogen is *P. falciparum*. In other embodiments, for example, the pathogen may be *P. vivax, P. ovale*, or *P. malariae*. Likewise, the method of the invention may be used with any malaria antigen expressed at any stage of the pathogen's lifecycle. In one embodiment, the priming vaccine encodes and the boosting vaccine comprises one or more antigens expressed during the pre-RBC stage of the pathogen, including the liver stage. In yet another embodiment, the polynucleotide of the priming vaccine encodes at least a portion of the circumsporozoite protein and the boosting vaccine comprises at least a portion of the circumsporozoite protein, which is expressed during the liver stage of infection. In still another embodiment, the polynucleotide of the priming vaccine encodes substantially all of the circumsporozoite protein and the boosting vaccine comprises a portion of the circumsporozoite protein. The minimum portion of the CS protein is an immunogenic portion comprising at least one epitope or several epitopes. In one specific embodiment, the priming vaccine comprises PfCSP and the boosting vaccine comprises RTS,S. In another embodiment, the priming vaccine is the PfCSP vaccine and the boosting vaccine is the RTS,S vaccine.

The invention further provides a pharmaceutical kit comprising the priming and boosting vaccines as described herein.

The invention further provides the use of a priming vaccine and a boosting vaccine as described herein, in the preparation of a vaccine for prevention or reduction of severity of malaria.

Thus the invention provides the use of a polynucleotide encoding at least one malaria antigen, in particular the CS protein or a fragment thereof, as a priming vaccine and a polypeptide comprising the at least one malaria antigen, in particular CS protein or a fragment thereof, as a boosting vaccine, in the manufacture of a prime-boost vaccine for malaria. In one specific embodiment, one polynucleotide is in the form of a DNA plasmid, preferably expressing full length CS protein or a fragment thereof. The polynucleotide encoding the CS protein or fragment may be under the control of a heterologous promoter as known in the art. In one embodiment, the promoter is the HCMV IE promoter, optionally including exon 1. In one specific embodiment, the polypeptide of the boosting vaccine is a hybrid protein comprising the carboxy terminal portion of the CS protein, for example at least 160 amino acids from the carboxy terminal portion, optionally excluding 12 amino acids from the carboxy terminus. Either or both of the priming and boosting compositions may comprise additional malaria antigens or other antigens.

In an embodiment according to this aspect of the invention, the priming vaccine comprises a polynucleotide encoding the full length CS protein, present in a DNA plasmid under the control of a heterologous promoter and the boosting vaccine comprises RTS,S in combination with a Th1 inducing adjuvant, particularly an adjuvant which comprises QS21, 3D-MPL and an oil in water emulsion. The priming and boosting vaccines may be provided in the form of a pharmaceutical kit.

The invention provides partial, enhanced, or full protection of a human who has not previously been exposed to a malaria-causing pathogen, or has been exposed, but is not fully protected. The invention may also be used to reduce the chance of developing a malaria infection, reduce the chance of becoming ill when one is infected, reduce the severity of the illness, such as fever, when one becomes infected, reduce the concentration of parasites in the infected person, or to reduce mortality from malaria when one is exposed to malaria parasites. In regions where malaria is endemic, even partial protection is beneficial. For example, a vaccine treatment strategy that results in protection of about 30% of a population may have a significant impact on a community.

IFN-γ responses were significantly reduced by CD4$^+$ and CD8$^+$ T cell depletion prior to culture after the first dose of RTS,S (a feature of DNA-induced IFN-γ responses). After the second dose of RTS,S vaccine, only CD4+ T cell depletion significantly reduced activity. In parallel, in the effector phase by real-time PCR (b), IFN-γ mRNA expression was up-regulated in CD8$^+$ but not in CD4$^+$ T cells after the first dose of RTS,S, and was up-regulated in both CD8$^+$ and CD4$^+$ T cells after the second dose of RTS,S. "2wkp1" refers to 2 weeks after the first dose and "2wkp2" refers to 2 weeks after the second dose.

Figure 5:
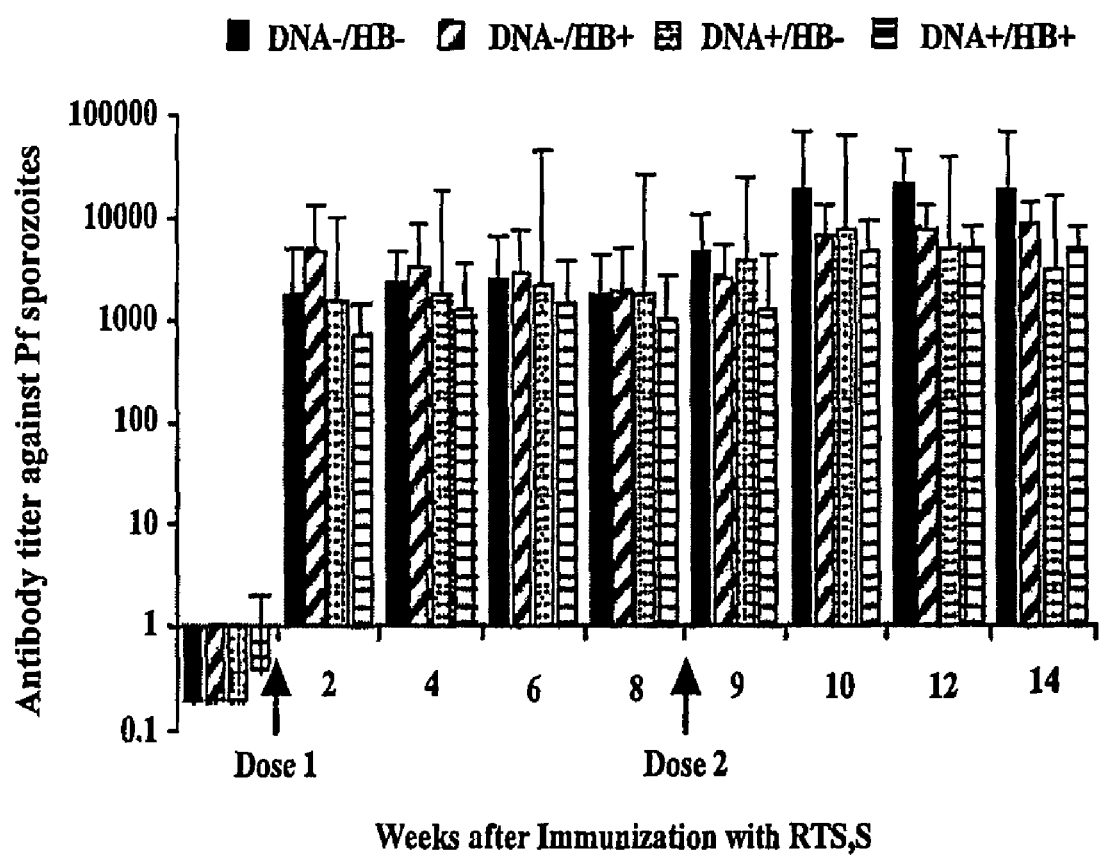

FIG. 5 shows the antibody IFAT titers of DNA-primed/RTS,S-boosted Volunteers. Antibody titers presented as geometric mean±SE (95% confident intervals) in DNA primed (+) and unprimed (−) volunteers with (+) and without (−) antibodies to HBsAg prior to first dose of RTS,S. Antibody assays were performed after the $1^{st}$ and $2^{nd}$ immunizations with RTS,S. There were no significant differences in titers between any of the groups, except that at 2 wks after the first dose, the DNA−/HBsAg+ volunteers had a significantly greater titer than did the DNA+/HBsAg+ (P<0.02).

DETAILED DESCRIPTION OF THE INVENTION

As demonstrated herein, a multiarmed immune response to malaria infection is primed by immunizing human subjects with a priming vaccine comprising a polynucleotide encoding at least one malaria antigen and then boosted by immunizing with a boosting vaccine comprising at least one polypeptide which comprises at least one malaria antigen having at least one epitope in common with the malaria antigen or antigens of the priming vaccine. Surprisingly, the instant immunization method boosts and broadens the primed response, using a polypeptide vaccine.

A "vaccine" is a composition of matter comprising a molecule that, when administered to a subject, induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art (83).

Any method or route of inoculation may be used alone or in combination to deliver the polynucleotide vaccine or the protein vaccine to a human subject. Routes of administration include intravenous, intramuscular, subcutaneous, intradermal or mucosal. Means of delivery may vary, for example, one may inject a human via an IV, IM, subcutaneously, or ID route. One may also inoculate a human subject via the mucosal route. Alternatively, delivery may be via a needleless means, such as using a needleless "gene gun" e.g., Biojector® or other jet injection device, or biolostic delivery. The polynucleotide may be delivered in bacteria comprising the DNA of the PfCSP vaccine, or viruses comprising the DNA of the PfCSP vaccine.

Examples of suitable viral vectors include herpes simplex viral vectors, vaccinia or alpha-virus vectors and retroviruses, including lentiviruses, adenoviruses and adeno-associated viruses. In one embodiment, these vectors are replication defective virus vectors. Gene transfer techniques using these viruses are known to those skilled in the art. Retrovirus vectors, for example, may be used to stably integrate the polynucleotide of the invention into the host genome, although such recombination may not be advisable. Replication-defective adenovirus vectors by contrast remain episomal and therefore allow transient expression.

In a specific embodiment, the adenovirus used as a live vector is a replication defective human or simian adenovirus. Typically these viruses contain an E1 deletion and may be grown on cell lines that are transformed with an E1 gene. Suitable Simian adenoviruses are, for example, viruses isolated from Chimpanzee. Examples of viruses suitable for use in the present invention include C68 (also known as Pan 9) (U.S. Pat. No. 6,083,716, incorporated herein by reference) and Pan 5, 6 and Pan 7 (WO 03/046124 incorporated herein by reference). Thus, these vectors can be manipulated to insert a heterologous gene of the invention such that the gene product maybe expressed. The use formulation and manufacture of such recombinant adenoviral vectors is set forth in detail in WO 03/046142, which is incorporated by reference.

A vaccine may be comprised of separate components. As used herein, "separate components" refers to a situation wherein the term vaccine actually comprises two discrete vaccines to be administered separately to a subject. In that sense, a vaccine comprised of separate components may be viewed as a kit or a package comprising separate vaccine components. For example, in the context of the instant invention, a package may comprise a polynucleotide vaccine component and a polypeptide vaccine component.

A vaccine "induces" an immune response when the antigen or antigens present in the vaccine cause the vaccinated subject to mount an immune response to that antigen or antigens. The vaccinated subject will generate an immune response, as evidenced by activation of the immune system, which includes the production of vaccine antigen-specific T cells, vaccine antigen-specific B cells, vaccine antigen-specific antibodies, and cytokines. The resulting immune response may be measured by several methods including ELISPOT, ELISA, chromium release assays, intracellular cytokine staining, FACS analysis, and MHC tetramer staining (to identify peptide-specific cells). A skilled artisan may also use these methods to measure a primary immune response or a secondary immune response.

An "antigen" is a substance capable of generating an immune response in a subject exposed to the antigen. Antigens are usually polypeptides and are the focus of the host's immune response. An "epitope" or "antigenic determinant" is that part of an antigen to which T cells and antibodies specifically bind. An antigen may contain multiple epitopes.

The priming vaccine used in the method of the invention comprises a polynucleotide encoding a malaria antigen, discussed below. The priming vaccine may be DNA alone or DNA that is under control of a foreign promoter within a bacterium or virus. The polynucleotide of the priming vaccine is present in a suitable delivery vector such as a plasmid or other vector such as a bacterial or viral vector. The polynucleotide may be under the control of a suitable promoter such as a promoter derived from the HCMV IE gene. The priming vaccine is administered in an amount effective for priming an immune response to the malaria antigen. As used herein, "priming" of an immune response occurs when an antigen is presented to T cells or B cells. As a result, primed cells can respond to the same antigen again as memory cells in a second, subsequent immune response. Thus, priming generates both the primary immune response and establishes immunological memory. One skilled in this art appreciates that a primary immune response represents the adaptive immune response upon initial exposure to an antigen in a particular context such as in the pathogen or in a vaccine. However, it will also be appreciated that the invention is not limited to use of the priming vaccine in the context of immunologically naïve individuals. Rather, priming may also occur in individuals who have been exposed to the antigen but who have not received the priming vaccine.

An "effective" priming dosage may range between 0.01 µg and 50 mg of DNA. Alternatively, the dosage may be between 1 µg and 10 mg of DNA or 2.5 mg and 5 mg of DNA. The polynucleotide vaccine may be administered once before administration of the boosting polypeptide vaccine. In another embodiment, the priming vaccine may be administered several times. An "effective" number of inoculations may range between 1 and 5 doses. Alternatively, the number of dosage may be between 1 and 3 doses or 1 and 2 doses before administering the boosting vaccine.

"Polynucleotide" generally refers to any polyribonucleotide (RNA) or polydeoxribonucleotide (DNA), which may be unmodified or modified RNA or DNA. Polynucleotides include, without limitation, single-stranded and double-stranded DNA, DNA that is a mixture of single-stranded and double-stranded regions, single-stranded and double-stranded RNA, and RNA that is a mixture of single-stranded and double-stranded regions. Polynucleotides also include hybrid molecules comprising DNA and RNA that may be single-stranded or, more typically, double-stranded or a mixture of single-stranded and double-stranded regions. In addition, "polynucleotide" refers to triple-stranded regions comprising RNA or DNA or both RNA and DNA. Polynucleotides also include DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. Oligonucleotides are relatively short polynucleotides.

A "fragment" of a polynucleotide sequence refers to a polynucleotide sequence that is shorter than the reference sequence but that retains a biological function or activity which is recognized to be the same as the reference polynucleotide. A fragment encodes at least one epitope of the reference polypeptide encoded by the reference polynucleotide sequence. As used herein, "substantially all" when used to describe a polynucleotide or polypeptide, refers to a molecule that, but for minor deletions of nucleotide bases or amino acid residues, encodes or represents the complete, full length polynucleotide or polypeptide.

The boosting vaccine used in the method of the invention may comprise a fusion protein comprising at least one malaria antigen polypeptide, discussed below. Polypeptides used in this vaccine may be isolated from a natural source, produced as a recombinant protein in a foreign organism such as bacteria, or synthesized via chemical means. The boosting vaccine may further comprise additional non-malarial polypeptides to enhance the immunogenicity of the malaria polypeptide. For example, one may use part or all of the Hepatitis B Virus surface antigen. The priming vaccine and the boosting vaccine share at least one common malaria epitope.

A suitable fusion protein for use in the boosting vaccine according to the invention may comprise a hybrid protein comprising substantially all the C-terminal portion of the CS protein, four or more tandem repeats of the immunodominant region, and the surface antigen from hepatitis B virus (HbsAg). The hybrid protein comprises a sequence which contains at least 160 amino acids which is substantially homologous to the C-terminal portion of the CS protein. In one embodiment, the CS protein may be devoid of the last 12 amino acids from the C terminus. A suitable hybrid protein comprises, for example, a portion of the CS protein of *P. falciparum* substantially as corresponding to amino acids 210-398 of *P. falciparum* 7G8 fused in frame via a linear linker to the N-terminal of HbsAg. The linker may comprise a portion of preS2 from HbsAg.

Another embodiment is the hybrid particle designated RTS,S which is described in U.S. Pat. No. 5,928,902 and in international patent application WO 93/10152, which are incorporated herein by reference. This hybrid is comprised of: 1.) a methionine-residue, encoded by nucleotides 1059 to 1061, derived from the *Saccharomyces cerevisiae* TDH3 gene sequence (71); 2.) three amino acids, Met Ala Pro, derived from a nucleotide sequence (1062 to 1070) created by the cloning procedure used to construct the hybrid gene; 3.) a stretch of 189 amino acids, encoded by nucleotides 1071 to 1637 representing amino acids 210 to 398 of the circumsporozoite protein (CSP) of *Plasmodium falciparum* strain 7G8 (21); 4.) an amino acid (Arg) encoded by nucleotides 1638 to 1640, created by the cloning procedure used to construct the hybrid gene; 5.) four amino acids, Pro Val Thr Asn, encoded by nucleotides 1641 to 1652, and representing the four carboxy terminal residues of the hepatitis B virus (adw serotype) preS2 protein (103); and 6.) a stretch of 226 amino acids, encoded by nucleotides 1653 to 2330, and specifying the S protein of hepatitis B virus (adw serotype).

The boosting vaccine is administered in an amount effective for "boosting" a primed immune response to the malaria antigen. As used herein, "boosting" an immune response means to induce a secondary immune response in a subject that has been primed (i.e., already exposed) by an initial exposure to an antigen. A secondary immune response is characterized by the activation and expansion of specific memory T cells and B cells. Thus, boosting a specific immune response augments the primed immune response by inducing immune cells to proliferate and differentiate upon subsequent exposure to that antigen. As discussed below, the full length CS protein of the PfCSP vaccine contains 9 T cell epitopes while RTS,S contains 5 T cell epitopes (61). Four of the RTS,S epitopes are present in the PfCSP vaccine. For example, when administered, the priming vaccine primes anti-malaria CD8+ T cells. The boosting vaccine may achieve one or more of the following effects: induces CD4+ T cells, induces anti-malaria antibodies, boosts the activity of the CD8+ T cells primed by the priming vaccine, and induces additional CD8+ T cells not originally identified in the initially primed immune response. The boosting vaccine may also induce CD4+ T cells and induce anti-malaria antibodies. Boosting an immune response is also known in the art as "recalling" the immune response.

An "effective" boosting dosage may range between 1 µg and 100 µg or between 10 µg and 75 µg or between 40 µg and 60 µg. In another embodiment, the boosting dosage may be 50 µg. In yet another embodiment, the boosting dosage may be 25 µg. The boosting vaccine may be administered once or multiple times. An "effective" number of boosting doses may range between 1 and 5 doses of the boosting vaccine. Alternatively, the number of doses may be between 1 and 3 doses or between 1 and 2 doses to a human subject. In another embodiment, both a DNA vaccine and protein vaccine may be used to boost the primary immune response.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than those normally encoded by a codon.

Polypeptides include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. Such modifications may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (79, 82, 94, 113).

A "fragment" of a polypeptide sequence refers to a polypeptide sequence that is shorter than the reference sequence but that retains a biological function or activity which is recognized to be the same as the reference polypeptide. Such an activity may include, for example, the ability to stimulate an immune response. A fragment retains at least one epitope of the reference polypeptide. A "portion" of a polypeptide refers to a subset of the amino acid sequence of the reference polypeptide. A portion may be described by its relative location in the polypeptide, for example, C-terminal portion or N-terminal portion.

The invention may be used with any malaria antigen, such as those shown in Table A and Table B.

TABLE A

| Pre-RBC Antigens | |
|---|---|
| ANTIGEN | REFERENCES |
| CSP | 13, 14, 29, 32, 41, 55 |
| | 66, 69, 78, 85, 87, 91, 99, 114 |
| SSP2 | 1, 13, 14, 29, 55, 56, 86, 104, 111, 112 |
| Exp1/Hep-17 | 15, 16, 27, 28, 29 |
| PfLSA1 | 29 and 44 |
| PfLSA3 | 22 |

TABLE B

| RBC Stage Antigens | |
|---|---|
| ANTIGEN | REFERENCES |
| MSP-1 | 7, 10, 12, 20, 34, 35, 46, 58, 59, 65, 95, 96 |
| MSP-2 | 3, 4, 17, 80, 81, 88 |
| MSP-3 | 72 and 73 |

TABLE B-continued

| RBC Stage Antigens | |
|---|---|
| ANTIGEN | REFERENCES |
| MSP-4 | 50 |
| MSP-5 | 7 |
| AMA1 | 5, 18, 19, 24, 25, 101, 102 |
| EBA175 region II | 97 and 98 |
| SERA | 26, 48, 49, 76, 77 |
| RAP2 | 39, 76, 84, 89 |

The "circumsporozoite protein" or "CSP" is the major surface Polypeptide on the surface of Malaria sporozoites. The CSP from *Plasmodium falciparum* (PfCSP) strain 7G8 has been cloned, sequenced and expressed (21). Other CSPs from other malaria parasites have also been characterized and are contained in Table A.

"RTS,S," as used herein, refers to a particular malaria antigen and represents one embodiment of the instant invention. RTS,S and its production is more fully described in U.S. Pat. No. 5,928,902 and international patent application WO 93/10152, which are both incorporated herein by reference.

"Broadening" refers to increasing the repertoire of T cell responses. In this case, a broader repertoire of IFN-γ-producing T cells (Tc1 and Th1) was induced by DNA-priming/RTS,S boost, since immunization/priming with DNA initiated both CD4$^+$ T cell-dependent CD8$^+$ type 1 (Tc1) and CD4$^+$ type 1 (Th1) IFN-γ responses, whereas RTS,S alone induced only CD4$^+$ T cell-dependent Th1 IFN-γ responses. A skilled artisan may detect a broadened immune response by using antigen-specific detection assays. For example, a skilled artisan may use an ELISPOT, MHC tetramer staining, or chromium release CTL assays to determine the repertoire of T cells.

"Broadening" also refers to increasing the range of epitopes to which an immune response will react. In addition to the immune cells initially primed, immune cells that were either not primed or in such small number as not to be detectable are also induced to expand and activate. Thus, a broadened immune response not only amplifies the originally primed response, it also contains responses to new epitopes that were not a part of the primary response. A skilled artisian may detect a broadened immune response by using antigen-specific detection assays. For example, a skilled artisan may use an ELISPOT or MHC tetramer staining to determine the repertoire of epitopes to which the primary immune response reacts and comparing that range to the repertoire of epitopes to which the secondary immune response reacts. If the secondary immune response reacts to a greater number of epitopes than the primary immune response, the secondary immune response has been broadened.

"CD8+ T cells" represent a class of T lymphocytes characterized by the possession of the CD8 cell surface marker. CD8+ T cells are MHC Class I-restricted "CTLs" or "suppressor T cells."

"CD4+ T cells" represent a class of T lymphocytes characterized by the possession of the CD4 cell surface marker. CD4+ T cells are MHC Class II-restricted T lymphocytes. There are two types of CD4+ T cells referred to as type 1 or type 2 "helper T cells."

As discussed above, an immune response is generated to an antigen through the interaction of the antigen with the cells of the immune system. The resultant immune response may be broadly distinguished into two extreme catagories, being humoral or cell mediated immune responses (traditionally characterised by antibody and cellular effector mechanisms of protection, respectively). These categories of response have been termed Th1-type responses (cell-mediated response), and Th2-type immune responses (humoral response). Extreme Th1-type immune responses may be characterised by the generation of antigen-specific, haplotype-restricted CTLs, and natural killer cell responses. In mice, Th1-type responses are often characterised by the generation of antibodies of the IgG2a subtype, while in the human these correspond to IgG1 type antibodies. Th2-type immune responses are characterized by the generation of a broad range of immunoglobulin isotypes including in mice IgG1, IgA, and IgM.

The driving force behind the development of these two types of immune responses is cytokines, a number of identified protein messengers which serve to help the cells of the immune system and steer the eventual immune response to either a Th1 or Th2 response. Thus, high levels of Th1-type cytolines tend to favor the induction of cell mediated immune responses to the given antigen, while high levels of Th2-type cytokines tend to favor the induction of humoral immune responses to the antigen. It is important to remember that the distinction of Th1 and Th2-type immune responses is not absolute. In reality, an individual will support an immune response which is described as being predominantly Th1 or predominantly Th2. However, it is often convenient to consider the families of cytokines in terms of that described in murine CD4+ T cell clones by Mosmann and Coffman (70). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumour necrosis factor-β (TNF-β).

Suitable adjuvants for use in the invention include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, polyphosphazenes, or montanide liposomes.

In the formulation of vaccines for use in the invention, in the context of the PfCSP plasmid, an adjuvant may or may not be administered. In the case of RTS,S, the adjuvant composition may induce a preferential Th1 response. Moreover, other responses, including other humoral responses, may also be induced.

Certain vaccine adjuvants are particularly suited to the stimulation of either Th1 or Th2-type cytokine responses. Traditionally, the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses. Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype. For example, Th1-type immunostimulants which may be formulated to produce adjuvants suitable for use in the present invention may include Monophosphoryl lipid A, in particular 3-de-O-acylated monophosphoryl lipid A (3D-MPL). 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099, 42, 43, EP 0 729 473 B1, EP 0 549 074 B1). In one embodiment, 3D-MPL is in the form of a particulate formulation having a small particle size less than 0.2 μm in diameter, and its method of manufacture is disclosed in EP 0 689 454.

Saponins are another example of Th1 immunostimulants that may be used with the invention. Saponins are well known adjuvants (60). For example, Quil A (derived from the bark of the South American tree Quillaja Saponaria Molina), and fractions thereof, are described in U.S. Pat. No. 5,057,540, EP 0 362 279 B1, and in Kensil (52). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (51). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Yet another example of an immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 96/02555, EP 468520, 23, 68). Historically, it was observed that the DNA fraction of bacillus Calmette-Guerin (BCG) could exert an anti-tumor effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated by Krieg (57). Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides, a palindromic sequence may be present. Several of these motifs, either as repeats of one motif or a combination of different motifs, can be present in the same oligonucleotide. The presence of one or more of these immunostimulatory sequences containing oligonucleotides can activate various immune subsets, including natural killer cells (which produce interferon γ and have cytolytic activity) and macrophages (Wooldrige et al., 1977). Other unmethylated CpG containing sequences not having this consensus sequence have also now been shown to be immunomodulatory. When formulated into vaccines, CpG is generally administered in free solution together with free antigen (WO 96/02555, 68) or covalently conjugated to an antigen (WO 98/16247), or formulated with a carrier such as aluminium hydroxide (Hepatitis surface antigen) (9, 23).

Such immunostimulants as described above may be formulated together with carriers, such as, for example, liposomes, oil in water emulsions, and or metallic salts, including aluminium salts (such as aluminium hydroxide). For example, 3D-MPL may be formulated with aluminium hydroxide (EP 0 689 454) or oil in water emulsions (WO 95/17210); QS21 may be advantageously formulated with cholesterol containing liposomes (WO 96/33739), oil in water emulsions (WO 95/17210) or alum (WO 98/15287); CpG may be formulated with alum (9, 23) or with other cationic carriers.

Combinations of immunostimulants may also be used, such as a combination of a monophosphoryl lipid A and a saponin derivative (WO 94/00153; WO 95/17210; WO 96/33739; WO 98/56414; WO 98/05355, WO 99/12565; WO 99/11241) or a combination of QS21 and 3D-MPL as disclosed in WO 94/00153. Alternatively, a combination of CpG plus a saponin such as QS21 may also be used in the present invention. Thus, suitable adjuvant systems include, for example, a combination of monophosphoryl lipid A, such as 3D-MPL, together with an aluminium salt. Another embodiment combines a monophosphoryl lipid A and a saponin derivative, such as the combination of QS21 and 3D-MPL as disclosed in WO 94/00153, or a less reactogenic composition where the QS21 is quenched in cholesterol containing liposomes (DQ) as disclosed in WO 96/33739. Yet another adjuvant formulation involving QS21, 3D-MPL and tocopherol in an oil in water emulsion is described in WO 95/17210. In another embodiment, CpG oligonucleotides are used alone or together with an aluminium salt. Examples of additional adjuvant and/or carrier combinations include: 3D-MPL+QS21 in DQ; Alum+3D-MPL; Alum+QS21 in DQ+3D-MPL; Alum+CpG; 3D-MPL+QS21 in DQ+oil in water emulsion; and CpG.

In another embodiment, 3D-MPL and QS21 are combined, with or without CpG. The ratio of QS21:3 D-MPL may be in the order of 1:10 to 10:1; 1:5 to 5:1; or 1:1. In one embodiment, the ratio is 2.5:1 to 1:1 D MPL:QS2 1. Typically for human administration QS21 and 3D MPL will be present in a vaccine in the range 1 pig–200 4 g, such as 1-1004 g, or 10~Lg-50~tg per dose. Typically the oil in water will comprise from 2 to 10% squalene, from 2 to 10% alpha tocopherol and from 0.33 to 3% tween 80. The ratio of squalene:alpha tocopherol is equal or less than 1 as this provides a more stable emulsion. Span 85 may also be present at a level of 1%. In some cases it may be advantageous that the vaccines of the present invention will contain a stabilizer.

Adjuvants for use with the polypeptide boosting vaccine according to the invention comprising the CS protein or an immunogenic portion thereof, optionally in a hybrid protein such as RTS,S, may comprise a combination of 3D-MPL and QS21 with or without CpG.

Both the foregoing general description and the following detailed description are exemplary and explanatory only and are not restrictive of the invention, as claimed. Moreover, the invention is not limited to the particular embodiments described, as such may, of course, vary. Further, the terminology used to describe particular embodiments is not intended to be limiting, since the scope of the present invention will be limited only by its claims.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The following examples further illustrate the invention. They are merely illustrative of the invention and disclose various beneficial properties of certain embodiments of the invention. The following examples should not be construed as limiting the invention.

EXAMPLES

Example 1

Boosting the Primed Anti-PfCSP Response with the RTS,S Vaccine

Twenty-four HLA-A*0201-positive volunteers were recruited for this study. The HLA diversity of the volunteers was restricted to the most common HLA Class I sub-type in this population in order to permit intergroup comparisons of genetically restricted T cell responses. None of these volunteers were previously exposed to malaria. Of these 24 individuals, 10 participated in the second PfCSP vaccine clinical trial described above. During that trial, these volunteers had received a total of three doses of the PfCSP DNA vaccine (VCL-2510, manufactured by Vical, Inc (San Diego, Calif.) as described previously (62)), given as 2500 µg per dose at 4-week intervals (62). Thus, in this trial, these 10 volunteers received their last dose of the DNA vaccine 12 to 14 months prior to receiving the boosting RTS,S vaccine. The remaining fourteen volunteers had not previously received the PfCSP DNA vaccine and were thus used as non-primed controls. All 24 volunteers were negative for antibodies to PfCSP, HIV, HBV core antigen, HCV, Vaccinia Virus, and dsDNA prior to immunization with both the PfCSP DNA vaccine and the RTS,S vaccine. Six of the 10 DNA-primed volunteers and 8 of the 14 non-primed controls were positive for antibodies to HBsAg.

All 24 volunteers received two injections of RTS,S vaccine at 0 and 8 weeks by intramuscular injection in the left deltoid. The RTS,S vaccine contained amino acids 207 to 395 of *Plasmodium falciparum* (NF54/3D7) CSP protein fused to hepatitis B surface antigen (HBsAg) (8). Briefly, the RTS,S protein is a hybrid protein comprising substantially all the C-terminal portion of the CS protein, four or more tandem repeats of the immunodominant region, and HBsAg. For a general description of preparing RTS,S, see WO 93/10152 and U.S. Pat. No. 5,928,902, which are incorporated herein by reference.

The resulting recombinant RTS,S protein was expressed in yeast (99) and was combined with the immune stimulants monophosphoryl lipid A and QS21 in an oil-in-water emulsion (Glaxo SmithKline Inc, Rixensart, Belgium) to make the RTS,S vaccine. Specifically, the lyophilized formulation contained an RTS,S pellet and an adjuvant diluent. The pellet contained RTS,S (50 μg) and lactose (3.15%) as a cryoprotectant. The adjuvant diluent contained MPL (50 μg), QS-21 (50 μg), and an oil/water emulsion. The resulting vaccine formulations contained 50 μg of RTS,S in a 1 ml volume of emulsion and were prepared 30 minutes before injection. Three HLA-mismatched volunteers did not receive the PfCSP DNA vaccine or RTS,S vaccine. Samples from these three volunteers were used as negative controls in the assays. One volunteer in the non-primed group withdrew from the study after the first immunization.

There were a number of T cell epitopes contained in the upstream region of the full-length PfCSP sequence, included in the PfCSP DNA vaccine, which were not present in the RTS,S vaccine. But there was enough overlap between the two vaccines to justify administering the RTS,S vaccine as a potential "boosting" vaccine to the volunteers previously immunized with the PfCSP DNA vaccine. Specifically, RTS,S includes a portion of PfCSP containing a highly conserved region of 19 NANP repeats and the carboxy terminus of CSP fused to the hepatitis B virus surface antigen (HBsAg) coexpressed in yeast with unfused HBsAg (36). The fall length CS protein of the PfCSP vaccine contains 9 T cell epitopes while RTS,S contains 5 T cell epitopes (61). Four of the RTS,S epitopes are present in the PfCSP vaccine.

Examples 2-7 detail the analyses that were subsequently performed on blood samples taken from each of the volunteers. Briefly, T cell responses were studied at 12-14 months after the last dose of PfCSP DNA vaccine for those volunteers who received priming with the PfCSP DNA vaccine and at 1, 2, and 6 weeks after the first and second dose of RTS,S vaccine for all volunteers. Antibodies were tested pre-immunization and at 2, 4, 6, and 8 weeks after each dose of RTS,S vaccine.

Example 2

CTL Responses

As discussed above, immunization with the RTS,S vaccine alone induces antibody and CD4$^+$ T cell-dependent IFN-γ responses in humans, but has not been reported to elicit antigen-specific CTLs in humans (61). To determine whether DNA-induced memory CTLs could be recalled by boosting with the RTS,S vaccine and whether the boosted response was broader than the original DNA primed response, the cytotoxic activity of antigen-specific CTLs in different volunteers was assessed. Peripheral blood mononuclear cells (PBMCs) were collected from the blood of DNA-primed or non-primed volunteers 1-2 weeks before immunization with RTS,S, and 1 or 2 weeks after the first and/or second doses of RTS,S. These PBMCs were then used in a chromium release assay, which detects the lysis of antigen-presenting target cells (105).

The in vitro chromium release assays were performed as previously described (105). Specifically, to generate effector cells, 20% of the total PBMCs were infected with ALVAC expressing the PfCSP (vCP182) at 5 pfu/cell for 90 min at 37° C. After washing twice, these PBMCs were combined with the remaining PBMCs, and cultured for 7-10 days. Recombinant human IL-2 (Cetus, Emeryville, Calif.) was added after 48 hours (20 U/ml). Target cells were autologous or MHC-mismatched PHA blasts that were sensitized overnight with PfCSP-specific CTL epitopes or control peptide at 10 μg/ml. The CTL activity was assessed by a conventional 6-hour chromium release assay. Percent lysis was defined as (experimental release−medium control release)/(maximum release−medium control release)×100. Percent specific lysis was determined by subtracting the percent lysis of targets cultured with the negative control HIV gag A2-restricted peptide from the percent lysis of targets incubated with the experimental peptide. CTL responses were considered positive only if the percent specific lysis post-immunization was ≧10% for at least two effector:target (E:T) ratios in the same assay and if percent specific lysis pre-immunization was <10%.

Synthetic peptides, at 80-95% purity, were used for sensitization of CTL targets and were obtained from Chiron Technologies (Clayton Victoria, Australia). Eight peptides derived from PfCSP and included in RTS,S sequence were used. These eight peptides included 4 defined CTL MHC class I-restricted epitopes, that were 9-10 amino acids long. The 4 CTL epitopes were restricted by HLA-A*0201 (peptide A2.319; amino acid residues 319-327, YLNKIQNSL; SEQ. ID. NO. 1), -A*0101 (peptide A1.310; a.a. residues 310-319, EPSDKHIKEY; SEQ. ID. NO. 2), -A*0301 (peptide A3/11.336; a.a. residues 336-345, VTCGNGIQVR; SEQ. ID. NO. 3), and -B*3501 (peptide B35.353; a.a. residues 353-360, KPKDELDY; SEQ. ID. NO. 4). The other four peptides were DR-binding peptides DR.316 (a.a. residues 316-335, IKEYLNKIQNSLSTEWSPCS; SEQ. ID. NO. 5), DR.318 (a.a. residues 318-332, EYLNKIQNSLSTEW; SEQ. ID. NO. 6), DR.363 (a.a. residues 363-383, DIEKKICKMEKCSS-VFNVVNS; SEQ. ID. NO. 7), and DR.346 (a.a. residues 346-365, IKPGSANKPKDELDYANDIE; SEQ. ID. NO. 8), which were 15-20 amino acids long as described previously (107). A pool of 13 PfCSP-derived peptides and a pool of 20 HBsAg-derived peptides, 15 amino acids in length, were provided by Glaxo SmithKline Inc (Rixensart, Belgium). The amino acid sequences of the 13 PfCSP peptides were as follows: NEEPSDKHIKEYLNK (SEQ. ID. NO. 9), DKHIKEYLNKIQNSL (SEQ. ID. NO. 10), EYLNKIQNSLSTEWS (SEQ. ID. NO. 11), IQNSLSTEWS-PCSVT (SEQ. ID. NO. 12), STEWSPCSVTCGNGI (SEQ. ID. NO. 13), PCSVTCGNGIQVRIK (SEQ. ID. NO. 14), CGNGIQVRIKPGSAN (SEQ. ID. NO. 15), QVRIKPG-SANKPKDE (SEQ. ID. NO. 16), PGSANKPKDELDYEN (SEQ. ID. NO. 17), KPKDELDYENDIEKK (SEQ. ID. NO. 18), LDYANDIEKKICKME (SEQ. ID. NO. 19), DIEK-KICKMEKCSSVF (SEQ. ID. NO. 20), and ICKMEKCSS-VFNVVN (SEQ. ID. NO. 21). Peptides derived from the influenza matrix protein (residue 58-66, GILGFVFTL, HLA-A2.1; SEQ. ID. NO. 22), or tetanus toxin universal T helper epitope P30 (residue 947-969, FNNFTVSFWLRVP-KVSASHLET, DR- and DP-restricted; SEQ. ID. NO. 23) were used as positive controls (74). Peptides from HV gag protein (residue 77-85, SLYNTVATL, HLA-A2.1 restricted; SEQ. ID. NO. 24), or *P. falciparum* protein, Exp-1 (residue 82-96, sequence AGLLGNVSTVLLGGV, DR restricted; SEQ. ID. NO. 25) were used as negative controls.

Recalling DNA-Induced Memory CTLs by Boosting with RTS,S

Figure 1:
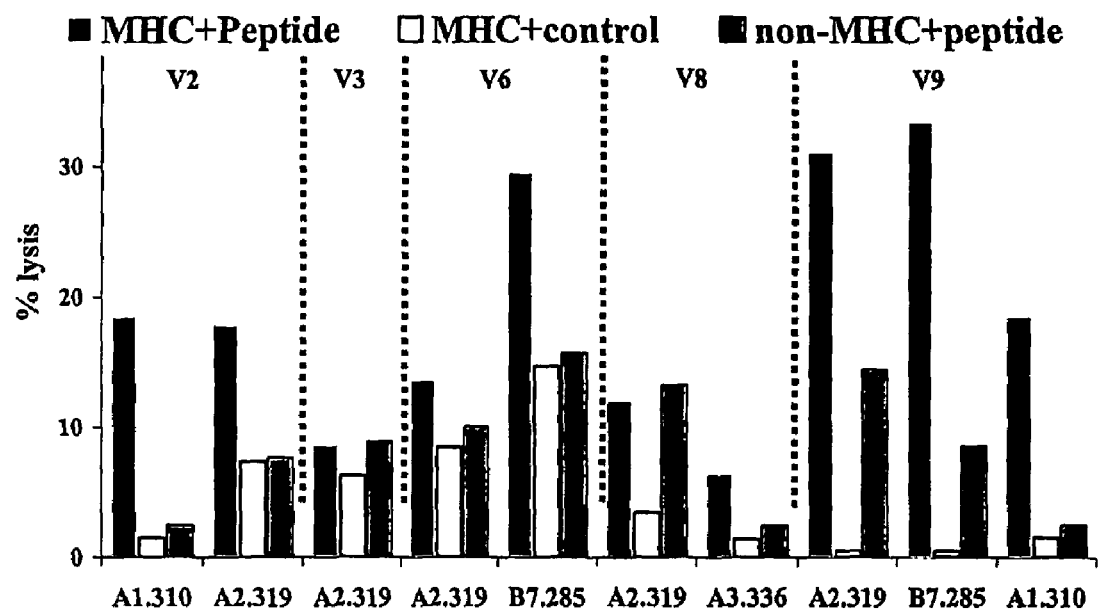
FIG. 1 shows CTL responses for each positive subject and each positive peptide just after DNA priming (FIG. 1a), just before boosting with RTS,S (FIG. 1b), and then after RTS,S boost (FIG. 1c). Black bars represent samples containing test peptide and the proper MHC presentation. Stippled bars represent samples containing a control peptide and the proper MHC presentation. Striped bars represent samples containing test peptide without proper MHC presentation. Fresh PBMCs taken after DNA priming (a), before boosting (b), or at 2 wks after the first (volunteer number 6=V6) or second (V2, 3, 8, and 9) dose of RTS,S (c), were stimulated in vitro with ALVAC expressing the PfCSP for 7 days, and assayed against HLA class I-matched (MHC+peptide) or -mismatched targets (Non-MHC+peptide) incubated with the experimental 8-10 amino acid PfCSP-derived peptide or control peptide [HLA-A*020] restricted HIV gag) (MHC+control), in a 5 hour chromium release assay. Responses were considered positive only if the difference between the percent lysis of target cells pulsed with experimental and control peptides was ≧10% for at least 2 effector cell to target cell ratios (E:T). The percent lysis for each peptide with its simultaneously assessed controls at a single E:T ratio (20:1 or 40:1) is provided.
Figure 1:
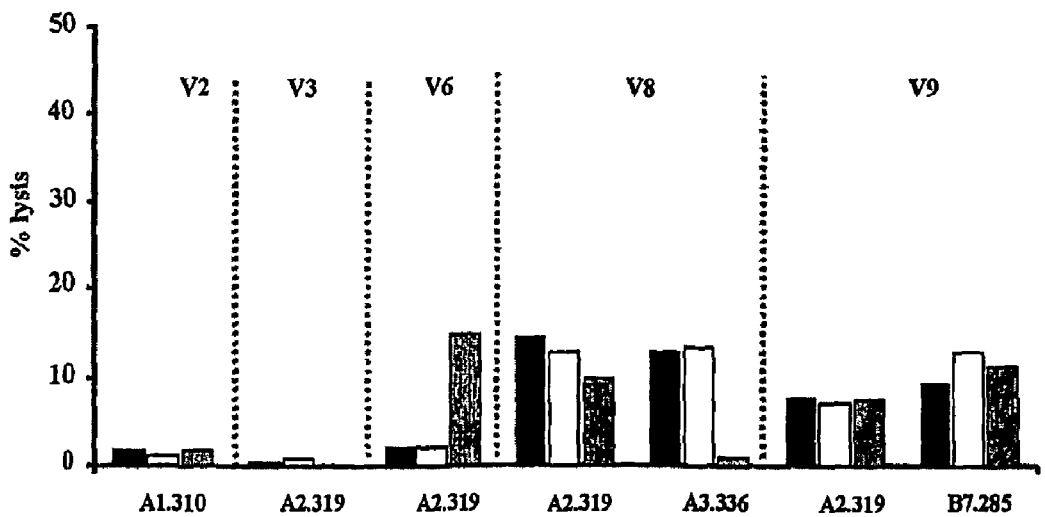
Figure 1:
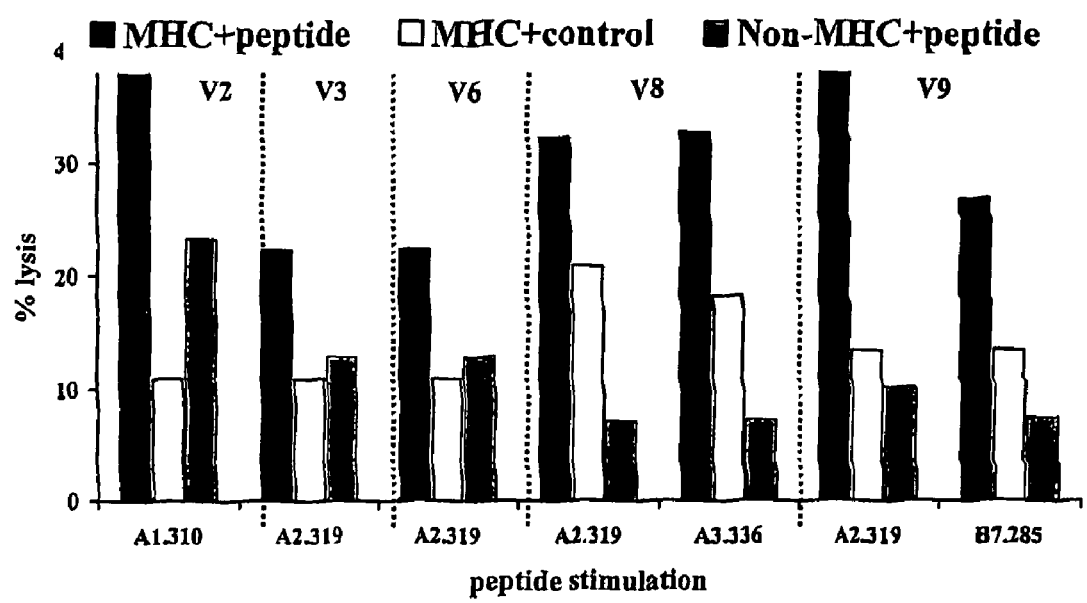

No CTLs were detected in DNA-primed or non-primed volunteers immediately prior to administration of the RTS,S vaccine. No CTL responses were detected in any of the 14 non-primed volunteers who received the RTS,S vaccine alone. Antigen-specific and genetically restricted CTL responses were detected in 5/10 DNA-primed volunteers (FIG. 1c). One of 5 responders had CTLs (V6) one week after the first dose, and the others had CTLs after the second dose of RTS,S. The frequency of CTL responses (7/113 assays, 6.2%) was significantly greater in the DNA-primed (P=0.0047) as compared to non-primed volunteers (0/125 assays, 0%). The frequency of CTL responses was comparable to that observed after DNA immunization alone among the 15 volunteers who received 3 doses of PfCSP DNA vaccine 12-14 months previously (30/458 assays, 6.6%) (107).

The magnitude of CTLs in the volunteers who had been primed with DNA and boosted with RTS,S (range of percent specific lysis [geomean]: 11.4-28.1 [15.4]) was also in the same range as that induced by DNA immunization alone (10.5-90.0 [15.6]). The RTS,S vaccine did not contain the CD8+ T cell epitopes associated with the highest prevalence of response in two previous studies (105, 107).

CTL responses to all 4 of the defined PfCSP-specific MHC class I-restricted epitopes, present in the RTS,S sequence, were detected. Of 5 CTL positive responders, 4 had CTLs to the HLA-A2-restricted epitope A2.319, one responded to the HLA-A1-restricted epitope A1.310 (V2), and 2/4 A2.319 responders also responded to the HLA-A3- and HLA-B7- restricted epitopes, A3.336 (V8), and B7.285 (V9) respectively. There were no detectable CTLs directed against the reported CD4$^+$ CTL epitope DR.318 (sequence E YLNKIONSLSTEWS; SEQ. ID. NO. 26) that contains the $\overline{CD8^+ CTL}$ epitope A2.319 (underlined) (69). There was also no detectable CTL activity in the 14 volunteers who had not received PfCSP DNA, but who did receive 2 doses of the RTS,S vaccine. The lack of CTL activity in these volunteers accords with previous studies that showed this vaccine alone was unable to induce CD8+ T cell activity (i.e., CTL activity).

Among the 5 DNA-primed volunteers who had positive CTL responses after boosting with the RTS,S vaccine, 3 did not have previously detectable CTL activity against the same epitopes when tested 2 and 6 wks after the second and third doses of PfCSP DNA immunization (107), approximately one year prior to the RTS,S boost. In contrast, two of the five volunteers previously had detectable CTL activity against peptides included within RTS,S after DNA immunization alone. These two volunteers did not respond to the RTS,S boost.

The RTS,S Boosted CTL Response is Broader than the DNA Primed CTL Response

Of the 5 DNA-primed volunteers who had positive CTL responses after boosting with the RTS,S vaccine, three of them (V3, V6, and V8) responded to epitopes after RTS,S boosting that had not been responded to after DNA priming. Specifically, CTL responses were considered positive only if the percent specific lysis post-immunization was ≧10% over the background of both negative controls (MHC+control and non-MHC+peptide). In V3 and V6, there was no CTL response to epitope A2.319 after DNA priming with the PfCSP vaccine (FIGS. 1a and 1b). After boosting with RTS,S, however, both volunteers did show a CTL response to this epitope (FIG. 1c). V8 did not have CTL responses to epitopes A2.319 and A3.336 after DNA priming, yet after boosting this primed volunteer with RTS,S vaccine, CTL responses to these epitopes appeared (FIGS. 1a, 1b, and 1c).

As discussed above, those in the art did not consider protein-based vaccines to be effective at stimulating CTL responses. Likewise, RTS,S, a protein-based vaccine, was heretofore considered ineffective at stimulating CD8+ T cell responses (61). In contrast to what was known, the above data clearly demonstrate that after DNA priming RTS,S can stimulate CTL responses to new CTL epitopes.

The frequency and magnitude of peptide-specific IFN-γ (below) and CTL responses was analyzed using the Chi Squared test, Fisher's exact test (two-tailed), or the Student's t-test (two-tailed). The t-test for paired sample was used for comparing the proportion of IFN-γ mRNA expression levels in T cell subpopulations. The level of significance was a p value<0.05.

Example 3

T Cell IFN-γ Responses to PfCSP

IFN-γ responses were evaluated by standard ELISPOT assays as follows. The number of PfCSP-specific IFN-γ-producing cells was determined by ELISPOT after 36 h in vitro stimulation in the presence of 10 μg/ml of peptides as previously described (107). The number of spots corresponding to cytokine producing cells in wells (spot forming cells; SFCs) were enumerated with an automated spot counting system (Scanalytics, Fairfax, Va.). Responses were expressed as the mean number of SFCs/10$^6$ PBMCs, and were considered significant if 1) the mean number of cells in wells with experimental peptide was significantly greater (p<0.05, student's T test) than in wells with control peptide; 2) the net SFCs/well (mean SFCs in experimental peptide wells minus the mean SFCs in control peptide wells) was ≧5 SFCs/well; and 3) stimulation index (the ratio of mean SFCs in experimental peptide wells to mean SFCs in control peptide wells) was greater than 2.0. Furthermore, if cells obtained prior to immunization had a positive response to a PfCSP-specific peptide as defined above, the response to the same peptide after the immunization was not considered positive.

As used herein, the "frequency of positive responders" in an IFN-γ ELISPOT is the number of volunteers that test positive for a particular peptide divided by the total number of volunteers in the test group. The "frequency of positive IFN-γ ELISPOT assays" is the number of positive reactions to a peptide divided by the total number of tests run on that peptide. For example, if 6 peptides are tested in each of 10 volunteers, the total number of tests is 60. If 36 of those tests are positive, then the frequency of positive assays is 36 out of 60. The "magnitude of an IFN-γ response" is indicated by the number of SFCs per one million PBMCs.

PBMCs, isolated 1-2 weeks prior to, and 1, 2, and 6 weeks after, the first and second doses of the RTS,S vaccine were used in the ELISPOT assay. In these assays, PBMCs were incubated with 8 defined PfCSP peptides, as discussed in Example 2, (four 9 amino acid peptides containing HLA class I-restricted epitopes, and four 15-20 amino acid peptides, each of which included a class II-restricted epitope, and three of which also contained a class I restricted epitope) and a pool of 13 PfCSP peptides which are included in the RTS,S sequence. These peptides are also discussed in further detail in Example 2 above.

DNA-primed or non-primed volunteers had no detectable PfCSP-specific IFN-γ responses prior to RTS,S immunization. There were no IFN-γ responses detected at any time after immunization in assays using only the 9 amino acid peptides having containing only MHC class I restricted epitopes. These are the same peptides discussed in Example 2. After the first dose, positive IFN-γ responses were detected for all four 15-20 amino acid PfCSP peptides in 6 of 10 DNA-primed volunteers compared to one such peptide in 2 of 14 non-primed volunteers (p=0.019) (Table 1). Positive responders are those who responded to at least one of the four peptides. Moreover, responders in the primed group responded to all four peptides tested while the responders in the non-primed group responded to only one of the four peptides tested. The frequency of responses was significantly greater in DNA-primed as compared with non-primed volunteers (positive assays/total assays: 20/116 [18.1%] vs. 4/164 [2.4%], p=0.00001) regardless of the individuals' HBsAg Ab status (Table 1).

teers as evidenced by the frequency of positive assays. The number of positive assays was significantly greater in DNA-primed than in non-primed volunteers among HBsAg antibody-positive individuals (23/72 [31.9%] vs. 11/84 [13.1%], p=0.0078), but not in HbsAg antibody negative individuals (37.5% vs. 40.3% positive assays) after the second RTS,S immunization.

At the epitope level, IFN-γ responses against peptides DR.316, DR.318, and DR.363 were compared between the DNA-primed and non-primed groups. DR.316 and DR.318 contain overlapping $CD4^+$ and $CD8^+$ T cell epitopes while DR363 contains only a $CD4^+$ T cell epitope (107).

TABLE 1

Overall frequency and magnitide of IFN-γ responses to PfCSP-specific peptides

| Group | number of responders/ number tested | | number of positive assays/ total assays (%) | | | range of net $SFC_s$/ $10^4$ PBMCs (geomean) | |
|---|---|---|---|---|---|---|---|
| | DNA-primed volunteers | non-primed volunteers | DNA-primed volunteers | non-primed volunteers | P value between two groups | DNA-primed volunteers | non-primed volunteers |
| after first immunization | | | | | | | |
| HBsAg (+) | 4/6 (66.7) | 2/8 (25.0) | 13/69 (18.8) | 4/95 (4.2) | 0.001 | 13.1-105.5 (38.5) | 20.0-63.1 (39.6) |
| HBsAg (−) | 2/4 (50.0) | 0/6 (0) | 7/47 (14.9) | 0/69 (0) | 0.0009 | 13.8-82.5 (32.7) | neg |
| Total | 6/10 (60.0)* | 2/14 (14.3)* | 20/116 (18.1) | 4/164 (2.4) | <0.00001 | 13.1-105.5 (36.3) | 20.0-63.1 (39.6) |
| after second immunization | | | | | | | |
| HBsAg (+) | 5/6 (83.0) | 6/8 (75.0) | 23/72 (31.9) | 11/84 (13.1) | 0.0078 | 11.9-82.5 (32.1) | 14.4-96.9 (37.8) |
| HBsAg (−) | 3/4 (75.0) | 6/6 (100.0) | 18/48 (37.5) | 29/72 (40.3) | 0.76 | 11.7-122.5 (33.4) | 17.5-125.6 (41.0) |
| Total | 8/10 (80.0) | 11/14 (84.6) | 41/120 (34.2) | 40/156 (25.6) | 0.12 | 11.7-122.5 (32.6) | 14.4-125.6 (39.6) |
| overall | | | | | | | |
| HBsAg (+) | 5/6 (83.0) | 6/8 (75.0) | 36/141 (25.5) | 15/179 (8.4) | 0.00003 | 11.9-105.0 (34.3) | 14.4-96.9 (38.1) |
| HBsAg (−) | 3/4 (75.0) | 6/6 (100.0) | 25/95 (26.3) | 29/141 (20.6) | 0.3 | 11.7-122.5 (33.2) | 17.5-125.6 (41.0) |
| Total | 8/10 (80.0) | 11/14 (84.6) | 61/238 (25.6) | 44/320 (13.8) | 0.0004 | 11.7-122.5 (33.9) | 14.4-125.6 (39.6) |

*after the first immunization, number of positive responders in DNA-primed volunteers was significantly greater than that in non-printed volunteers (6/10 vs. 2/14, p = 0.019)

After the second dose of the RTS,S vaccine, IFN-γ responses were detected in 8 of 10 DNA-primed volunteers and in 11 of 14 non-primed volunteers (Table 1). Although there was no difference between the two groups in terms of number of responders after the second dose of the RTS,S vaccine (see number of positive assays/total assays (%)), there was a statistically significantly greater number of overall positive assays among the DNA-primed as compared to the non-primed volunteers (positive assays/total assays, 61/238 [25.6%] vs. 44/320 [13.8%], p=0.0004) (Table 1). This difference in numbers of overall positive assays was directly related to the HbS Ag antibody status of the volun- As set forth in Table 2, IFN-γ responses against peptide DR.316 were detected in 4 of 10 DNA-primed as compared to 0 of 14 in non-primed volunteers after the first dose of the RTS,S vaccine (p=0.0095), and in 6 of 10 DNA-primed compared to 5 of 13 in non-primed volunteers after the first and second doses of the RTS,S vaccine (p=0.35). When all assays were considered overall (after the first and second doses of the RTS,S vaccine), the DNA primed group had a greater frequency of positive assays (positive assays/total assays, 17/60 vs. 8/81, p=0.0046), but there was no difference in the magnitude of IFN-γ responses (range of SFCs: 11.9-106.3 [33.0] vs. 17.5-58.1 [28.4], p=0.21).

TABLE 2

Frequency of IFN-γ responses against PfCSP at the epitope level

| Group | number of responders/ number tested (%) | | | number of positive assays/ total assays (%) | | |
|---|---|---|---|---|---|---|
| | DR.316 | DR.318 | DR.363 | DR.316 | DR.318 | DR.363 |
| after first immunization | | | | | | |
| DNA-primed | 4/10 (40) | 3/10 (30.0) | 3/10 (30.0) | 6/30 (20.0) | 4/30 (13.3) | 4/30 (13.3) |
| Non-primed | 0/14 (0) | 0/14 (0) | 2/14 (14.3) | 0/42 (0) | 0/42 (0) | 2/42 (4.8) |

TABLE 2-continued

Frequency of IFN-γ responses against PfCSP at the epitope level

| Group | number of responders/ number tested (%) | | | number of positive assays/ total assays (%) | | |
|---|---|---|---|---|---|---|
| | DR.316 | DR.318 | DR.363 | DR.316 | DR.318 | DR.363 |
| P value | 0.0095 | 0.028 | 0.35 | 0.0025 | 0.015 | 0.195 |
| | | | after second immunization | | | |
| DNA-primed | 5/10 (50.0) | 6/10 (60) | 2/10 (20) | 11/30 (36.7) | 10/30 (33.3) | 4/30 (13.3) |
| Non-primed | 5/13 (38.5) | 1/13 (7.7) | 7/13 (54) | 8/39 (20.5) | 1/39 (20.5) | 16/39 (41.0) |
| P value | 0.58 | 0.0069 | 0.099 | 0.136 | 0.00054 | 0.012 |
| | | | overall | | | |
| DNA-primed | 6/10 (60) | 6/10 (60) | 4/10 (40) | 17/60 (28.3) | 14/60 (23.3) | 8/60 (13.3) |
| Non-primed | 5/13 (38.5) | 1/13 (7.7) | 9/14 (64) | 8/81 (9.9) | 1/81 (1.2) | 18/81 (22.2) |
| P value | 0.35 | 0.0069 | 0.24 | 0.0046 | <0.0003 | 0.178 |

Also, as shown in Table 2, IFN-γ responses against peptide DR.318, which does not contain the first two amino acids of peptide DR.316, were detected in 3 of 10 DNA-primed compared to 0 of 14 in non-primed volunteers after the first dose of the RTS,S vaccine (p=0.028), and in 6 of 10 DNA-primed compared to 1 of 13 in non-primed volunteers after the first and second doses of the RTS,S vaccine (p=0.0069). ELISPOT assays performed after the first and second doses of the RTS,S vaccine overall showed that the DNA primed group had a greater frequency of positive assays (positive assays/total assays, 14/60 vs. 1/81, p<0.00003). Given that there was only a single response to this peptide in the group that only received the RTS,S vaccine, it was impossible to compare magnitude of responses.

IFN-γ responses against peptide DR.363, which does not contain a known CD8+ T cell epitope, were detected in 3 of 10 DNA-primed compared to 2 of 14 in non-primed volunteers after the first dose of the RTS,S vaccine (p=0.35), and in 4 of 10 DNA-primed compared to 9 of 14 non-primed volunteers overall after the first and second dose of the RTS,S vaccine (p=0.24) (Table 2). Assays done after the first and second doses of the RTS,S vaccine showed no significant difference between the DNA primed group and RTS,S alone group in frequency of positive assays (positive assays/total assays, 8/60 vs. 18/81, p=0.178). But there was a significantly greater magnitude of IFN-γ responses in non-primed as compared with DNA-primed volunteers after the second dose of RTS,S (range of SFCs: 13.1-58.8 [26.4 geometric mean] per $10^6$ cells vs. 14.0-140.6 [47.9 geometric mean] per $10^6$ cells, p=0.004).

Similarly, after two doses of the RTS,S vaccine, there was no difference in the frequency of positive responding individuals between the DNA primed group and RTS,S alone group (8/10 vs 11/13). See Table 1. Individuals in the DNA-primed group responded to significantly more of the peptides tested than did the volunteers who only received the RTS,S vaccine. Of the 8 responders in the 10 DNA-primed volunteers, one had responses against all four of the 15-20 amino acid peptides tested, one responded to three peptides, 5 to two peptides, and only one responded to one peptide. Of the 11 responders in the 13 non-primed volunteers, one responded to 3 peptides, two responded to 2 peptides and eight responded to only one peptide (2/8 responded to DR.316 and 6/8 responded to DR.363). Overall, 7 of 8 DNA-primed compared to 3 of 11 non-primed volunteers responded to at least two peptides tested (p=0.0094).

Example 4

T Cell IFN-γ Responses to HBsAg

RTS,S is a fusion protein of part of the PfCSP and hepatitis B surface antigen (HBsAg). Immunization with RTS,S in adjuvant was significantly less efficient in inducing T cell responses among individuals with antibodies to HBsAg. This effect was much less pronounced in DNA primed volunteers. Because of the noted influence of HBsAg antibody status on response to the four 15-20 amino acid peptides, we expanded the studies. IFN-γ responses to PfCSP and HBsAg were compared by conducting ELISPOT assays as described above with a pool of 13 PfCSP peptides (pPfCSP) and a pool of 19 HBsAg peptides simultaneously in PBMCs at all study time points after the first and second RTS,S immunization. In naïve, non-DNA primed, individuals, the HBsAg component was immunodominant for T cell responses (compare 0/6 responders for PfCSP to 6/6 responders for HBsAg for HBsAg negative, non-primed volunteers and 1/8 responders for PfCSP to 7/8 responders for HBsAg for HBsAg positive non-primed volunteers), but PfCSP DNA priming appeared to balance this immunodominance directing T cell responses toward PfCSP (Table 3; compare 2/4 responders for PfCSP to 2/4 responders for HBsAg for HBsAg negative, primed volunteers and 4/6 responders for PfCSP to 6/6 responders for HBsAg for HBsAg positive primed volunteers).

TABLE 3

Frequency and magnitude of IFN-γ responses between HBsAg seropositive and seronegative volunteers

| | DNA-primed volunteers | | | non-primed volunteers | | |
|---|---|---|---|---|---|---|
| response to peptide pool | HBsAg (+) | HBsAg (-) | P value | HBsAg (+) | HBsAg (-) | P value |
| Frequency [positive responders/total volunteers (%)] | | | | | | |
| after first immunization | | | | | | |
| pPfCSP | 4/6 (66.7) | 2/4 (50.0) | 0.6 | 1/8 (12.5) | 0/6 (0) | 0.37 |
| pHBsAg | 6/6 (100.0) | 2/4 (50.0) | 0.05 | 7/8 (87.5) | 6/6 (100.0) | 0.37 |
| P value | 0.12 | 1.00 | | 0.003 | 0.0005 | |
| after second immunization | | | | | | |
| pPfCSP | 5/6 (83.0) | 3/4 (75.0) | 0.75 | 3/7 (42.9) | 5/6 (83.0) | 0.14 |
| pHBsAg | 5/6 (83.0) | 3/4 (75.0) | 0.75 | 7/7 (100.0) | 6/6 (100.0) | — |
| P value | 1.00 | 1.00 | | 0.018 | 0.3 | |
| Frequency [positive assays/total assays (%)] | | | | | | |
| after first immunization | | | | | | |
| pPfCSP | 4/15 (26.7) | 2/11 (18.2) | 0.61 | 2/23 (8.7) | 0/15 (0) | — |
| pHBsAg | 12/15 (80.0) | 3/11 (27.3) | 0.007 | 16/23 (69.6) | 9/15 (60.0)* | 0.54 |
| P value | 0.0034 | 0.61 | | 0.00002 | — | |
| after second immunization | | | | | | |
| pPfCSP | 9/18 (50) | 7/12 (58.3) | 0.65 | 3/21 (14.3) | 12/18 (66.7) | 0.0008 |
| pHBsAg | 12/18 (66.7) | 7/12 (58.3) | 0.64 | 16/21 (76.2) | 17/18 (94.4)* | 0.12 |
| P value | 0.31 | 1.00 | | 0.00006 | 0.035 | |
| Magnitude [net SFCs/$10^6$ PBMCs (geomean)] | | | | | | |
| after first immunization | | | | | | |
| pPfCSP | 19.5-52.2 (33.7) | 53.1-82.5 (66.2) | 0.23 | 35.6-54.4 (44.0) | neg | — |
| pHBsAg | 13.5-80.0 (37.7) | 21.3-144.4 (46.0) | 0.54 | 13.1-222.9 (60.1) | 13.1-132.5 (33.9)* | 0.013 |
| P value | 0.41 | 0.78 | | 0.052 | — | |
| after second immunization | | | | | | |
| pPfCSP | 18.1-68.8 (33.8) | 11.7-122.5 (37.9) | 0.11 | 25.0-4.4 (37.6) | 17.5-125.6 (46.1) | 0.09 |
| pHBsAg | 18.8-131.3 (52.8) | 17.9-215.0 (57.6) | 0.34 | 20.0-278.8 (62.3) | 12.5-317.5 (97.3)* | 0.013 |
| P value | 0.024 | 0.29 | | 0.0032 | 0.0001 | |

*Both frequency and magnitude of IFN-γ responses against HBsAg in HBsAg seronegative volunteers from non-primed group was significantly increased after the second immunization compared to after the first immunization compared to after the first immunization and P values = 0.035 and 0.00003 respectively.

In non-primed volunteers, IFN-γ responses to HBsAg were high in all individuals regardless of whether or not they had antibodies to HBsAg (Tables 3 and 4; see non-primed volunteers). As shown in Table 3, after the first dose of the RTS,S vaccine, the magnitude of responses to the HbsAg peptide pool was significantly greater in individuals with pre-existing antibodies to HBsAg than in those without such antibodies (range of SFCs/$10^6$ PBMCs [geomean]: 13.1-222.9 [60.1] vs. 13.1-132.5 [33.9], p=0.013). After the second immunization with the RTS,S vaccine, however, there was no difference in the magnitude of INFγ between the two groups (see magnitude data). The responses to HBsAg in HBsAg antibody-negative individuals were significantly increased after the second dose of the RTS,S vaccine compared with after the first dose (Table 3). Specifically, the frequency of positive assays after two RTS,S vaccine doses was 17/18 compared to 9/15 after the first dose (p=0.035) (see footnote of Table 3). The magnitude of the IFN-γ response was 12.5-317.5 [geomean=97.3] compared to 13.1-132.5 [geomean=533.9] with only one dose (p=0.024) (see footnote of Table 3). After the second dose, the numbers of SFCs was significantly greater in HbsAg antibody-negative individuals, than in HBsAg antibody-positive individuals (12.5-317.5 [97.3] compared to 20.0-278.8 [62.3], p=0.013) (Table 3).

As Table 3 provides, IFN-γ responses to PfCSP showed a different pattern from the responses to HBsAg. Thirteen of fourteen non-primed volunteers responded to HBsAg after one dose of the RTS,S vaccine, as shown in 7 of 8 HBsAg positive volunteers and in all 6 HBsAg negative volunteers. In contrast, only one of these 14 individuals responded to PfCSP (p=0.0049), as shown in 1 of 8 of HBsAg positive volunteers and 0 of 6 HBsAg negative volunteers. Overall, RTS,S-induced IFN-γ responses were significantly lower to PfCSP than to HBsAg in all volunteers who were not primed with DNA, and even lower in individuals with pre-existing anti-HBsAg antibodies (Table 3), as measured by the frequency of positive responders and positive assays after the first and second doses of RTS,S. See the p values for non-primed volunteers. Likewise, the magnitude of IFN-γ responses was lower after each immunization in both HBsAg antibody-positive (p<0.05-0.0032) and antibody-negative individuals (p=0.0001) (Table 3). See highlighted p values in the magnitude section of Table 3. These data demonstrated that, in non-primed individuals, RTS,S elicited T cell responses to PfCSP and to HBsAg, the response to HBsAg being significantly more robust than the response to PfCSP (Table 4).

In DNA-primed volunteers who were also HbsAg antibody-positive, the number of positive assays after the first dose of RTS,S was greater to HBsAg than it was to PfCSP (12/15 vs. 4/15, p=0.0034) (Table 3). Upon administering the second dose of RTS,S vaccine, however, the frequency of positive assays to PfCSP was no different that the frequency for HBsAg in HBsAg antibody-positive volunteers. See frequency data for DNA primed volunteers. In DNA primed, HbsAg antibody-negative volunteers, these frequencies were not different after the first dose or second dose of the RTS,S vaccine. The magnitude of responses to PfCSP and HbsAg were similar after the first dose regardless of HbsAg antibody status (Table 3). But after the second dose in DNA primed, HBsAg antibody-positive individuals, the magnitude of responses to HBsAg was increased significantly as compared to the magnitude of responses to PfCSP (range of SFCs/$10^6$ PBMCs [geomean]: 18.1-68.8 [33.8] vs. 18.8-131.3 [52.8], p=0.024). These results indicated that responses to HBsAg may eventually predominate over the responses to PfCSP if multiple doses of the RTS,S vaccine are administered.

Example 5

DNA Vaccine Induces Both Tc1 (CD8$^+$) and Th1 (CD4$^+$) Type Responses Whereas RTS,S Induces Only Th1 Responses in Humans Either the PfCSP DNA vaccine or the RTS,S vaccine alone is capable of inducing IFN-γ responses, so that after the second dose of RTS,S vaccine, the IFN-γ responses in both groups were equivalent in terms of the positive responders (8/10 compared to 11/14) (Table 1). Nevertheless, as reported previously, the IFN-γ responses induced by the PfCSP DNA vaccine or RTS,S vaccine alone were dependent upon different subsets of T cells. Immunization with DNA induces both CD4$^+$ and CD8$^+$ T cell-dependent IFN-γ responses (107), and RTS,S induces only CD4$^+$ T cell-dependent responses (61).

T cell profiles of IFN-γ responses in both induction and effector phases in vitro were characterized by ELISPOT and real-time PCR respectively with PBMCs from the volunteers immunized with DNA alone, RTS,S alone, or from the DNA-primed/RTS,S-boosted volunteers.

ELISPOT assays were carried out with PBMCs depleted of CD4$^+$ or CD8$^+$ T cells prior to culture with peptides using anti-CD4$^+$- or anti-CD8$^+$-coated Dynabeads M-450 (Dynal, Inc., Great Neck, N.Y.). IFN-γ mRNA expression levels were measured by real-time PCR in selectively enriched T cell populations: CD4$^+$/CD45RA$^+$, CD4$^+$/CD45RA$^-$, CD8$^+$/CD45RA$^+$, and CD8$^+$/CD45RA$^-$ T cells. In these assays, frozen PBMCs were recovered by overnight culture in 24-well plate at 3×$10^6$ cell/well in 2 ml complete RPMI medium with 10% human AB serum, and then stimulated with short peptide (9-10 amino acid A2 peptide sequence GILGFVFTL; SEQ. ID. NO. 27) for 2 hours, or long peptides (15-20 amino acid) for 4 h at 10 µg/ml. Then, PBMCs were harvested and enriched for CD8$^+$ or CD4$^+$ T cells using MACS MultiSort kit, and then CD45RA$^+$ and CD45RA$^-$ cells were separated by passing the enriched CD4$^+$ or CD8$^+$ T cells through CD45RA MicroBeads (Miltenyi Biotec, Auburn, Calif.).

To quantify IFN-γ mRNA by real-time PCR, total RNA was isolated from enriched T cell subsets using the RNeasy kit (Qiagen, Valencia, Calif.). cDNA was synthesized from the total RNA using random hexamers and the TaqMan Reverse transcription kit (PE Applied Biosystems, Foster City, Calif.). A relative quantification of IFN-γ mRNA by real-time PCR was done on an ABI PRISM 7700 Sequence Detector (Perkin-Elmer) using TaqMan PCR kit according to manufacturer's instructions. The primers, probes and standards for amplifying the IFN-γ and GAPDH mRNA were designed and standardized in house. A relative quantification of IFN-γ mRNA by real-time PCR was done on an ABI PRISM 7700 Sequence Detector (Perkin-Elmer) using the TaqMan TM PCR kit according to manufacturer's instructions. The primers (hIFN-g-F, TTGGTGATGATTTGAA-CATTGGA, SEQ. ID. NO. 28; hIFN-g-R, CCCAGTTCCT-GCAGAGTAGAAAA, SEQ. ID. NO. 29; hGAPDH-F, 5'GAA GGTGAAGGTCGGAGTC, SEQ. ID. NO. 30; hGAPDH-R, GAAGATGGTGATGGGATTTC SEQ. ID. NO. 31), probes (hIFN-g probe: TGTCACTTG CAAACA-CACAGCTTGTCGAA, SEQ. ID. NO. 32; hGAPDH probe: CAAGCTTCCCGTTCTCAGCC, SEQ. ID. NO. 33) for amplifying the IFN-g and GAPDH mRNA were designed and standardized in house following the manufacturer's protocol. Amplification of GAPDH was done for each experimental sample as an endogenous control to account for differences in the amount and quality of total RNA added to each reaction. Thermal cycling conditions were 2 min at 50° C. and 10 min at 95° C., followed by 50 cycles of 2 step PCR consisting of 15 s at 95° C. and 1 min at 60° C. All samples were amplified in triplicate. Threshold cycle (Ct), which correlates inversely with the target mRNA levels, was measured as the cycle number at which the reporter florescent emission increased above a threshold level. Target gene expression was normalized between different samples based on the values of the expression of the GAPDH gene.

Depleted T cell populations were incubated with defined PfCSP peptides prior to the ELISPOT assays in order to identify which subsets of T cell were involved in the induction phase of IFN-γ responses in vitro. In parallel, IFN-γ mRNA expression levels were assessed by real-time PCR in enriched subsets of T cell populations after incubation of PBMCs with the same peptides used for the ELISPOT assays to delineate the effector T cells that actually secreted IFN-γ. Responses to peptide DR.363 (containing only a class II restricted CD4$^+$ T cell epitope) and DR.316 (containing overlapping class I and class II restricted CD4$^+$ and CD8$^+$ epitopes) were assessed to compare the mechanisms underlying the IFN-γ responses against PfCSP by different vaccine delivery systems. Responses to the HLA-A2-restricted, immunodominant and conserved CD8$^+$ T cell epitope from influenza matrix protein (Flu M A2) and the HLA-DR-restricted CD4$^+$ T cell epitope from tetanus toxin (TT-DR) were also evaluated in parallel to provide internal standardization between different epitopes, assays, and volunteers.

The in vitro induction of IFN-γ responses to the Flu M A2 peptide were CD8$^+$ but not CD4$^+$ T cell-dependent since depletion of CD8$^+$ but not CD4$^+$ T cells immediately before culture of PBMCs completely abrogated or significantly reduced IFN-γ responses in all 17 individuals tested, regardless of what type of anti-malaria vaccine they received (FIG. 2a). In contrast, the responses to peptide TT-DR were completely CD4$^+$, not CD8$^+$, T cell dependent, in all 3 positive responders tested (FIG. 2b).

IFN-γ mRNA expression levels measured by real-time PCR in 4 enriched T cell populations (CD4$^+$/CD45RA$^+$, CD4$^+$/CD45RA$^-$, CD8$^+$/CD45RA$^+$, and CD8$^+$/CD45RA$^-$) were consistent with the findings obtained from the ELISPOT assays. IFN-γ mRNA was up regulated predominantly in CD8$^+$ T cells after stimulation with the Flu M A2 peptide (FIG. 2e: standards). The IFN-γ mRNA expression levels increased 6.8 fold (range, 3.4-12.9 fold) in CD8$^+$ T cells compared to 2.2 fold (range, 0.98-7.58 fold) in CD4$^+$ T cells (p=0.03). The percentage of IFN-γ mRNA up-regulation in CD8+ over CD4+ T cells was 78% on average (range, 62-99%). In contrast, IFN-γ mRNA was up regulated predominantly in CD4$^+$ T cells after stimulation with TT-DR (FIG. 2e: standards). The IFN-γ mRNA levels increased 7.6 fold (range, 2.4-18.3) in CD4$^+$ T cells compared to 2.2 fold (range, 1.1-4.6) in CD8$^+$ T cells (p=0.02). IFN-γ mRNA up-regulation in CD4$^+$ T cells over CD8$^+$ T cells was 79% (range, 74-100%). These results indicated that CD8$^+$ T cells are functional effectors of IFN-γ responses against Flu M A2 peptide whereas CD4+ T cells are the effectors against TT-DR peptide.

Conducting the assays in parallel with two standards as described above, we clarified the T cell profiles of IFN-γ responses induced by the DNA PfCSP vaccine or the RTS,S vaccine to two different PfCSP peptides (DR.363 and DR.316). Consistent with the fact that peptide DR.363 contains a CD4+ T cell epitope, but not a CD8+ T cell epitope, the ELISPOT results with depleted T cell populations showed that the IFN-γ responses to peptide DR.363 were completely CD4+ T cell-dependent in volunteers who received the PfCSP DNA vaccine alone (2/2 tested, V1 and V5) or RTS,S alone (6/6 tested) (FIG. 2c). IFN-γ mRNA expression levels in enriched T cell populations were correlated with the T cell dependence by ELISPOT. IFN-γ mRNA was up regulated predominantly in CD4+ T cells in both PfCSP DNA- and RTS,S vaccine-immunized volunteers (FIG. 2e: DR.363). In five DNA-immunized volunteers tested, IFN-γ mRNA levels increased 5.3 fold (range, 2.6-11.5) in CD4+ T cells compared to a 1.7 fold (range, 0.99-3.2) in CD8+ T cells (p=0.014). IFN-γ mRNA up-regulation in CD4+ over CD8+ T cells was 74% (range, 64-91%). The same pattern was seen in four RTS,S-immunized volunteers tested (FIG. 2e), IFN-γ mRNA levels increased 9.2 fold (range, 2.9-53.5) in CD4+ compared to a 0.9 fold (range, 0.6-1.1) in CD8+ T cells, and that IFN-γ mRNA up-regulation in CD4+ over CD8+ T cells was 86% (range, 73-98%). These results provided the first evidence that the DNA PfCSP vaccine induced PfCSP-specific and CD4+ T cell-dependent, in addition to CD8+ T cell-dependent, IFN-γ responses in humans.

IFN-γ responses to DR.316 (overlapping CD4+ and CD8+ T cell epitope) were dependent upon different subsets of T cells in volunteers receiving either the PfCSP DNA vaccine or the RTS,S vaccine alone. The responses were both CD4+ and CD8+ T cell-dependent in volunteers who received DNA alone (V1) (FIG. 2d) as previously reported (107), compared to only CD4+, but not CD8+ T cell-dependent in volunteers who received the RTS,S vaccine alone (3/3 volunteers tested) (FIG. 2d). Furthermore, IFN-γ mRNA was up-regulated predominantly in CD8+ T cells in DNA-immunized volunteers (FIG. 2e: DR.316), although the response was both CD4+ T cell and CD8+ T cell dependent by ELISPOT.

IFN-γ mRNA expression levels increased 64.7 fold in CD8+ T cells compared to 0.36 fold in CD4+ T cells, and IFN-γ mRNA up-regulation in CD8+ over CD4+ T cells was 99.6%. In contrast, transcription of IFN-γ mRNA was up-regulated predominantly in CD4+ T cells in RTS,S vaccine-immunized volunteers (FIG. 2e: DR.316). IFN-γ mRNA expression levels increased 24.7 fold (range, 5.3-176.7 fold) in CD4+ T cells compared to 2.5 fold (range, 1.1-5.6 fold) in CD8+ T cells. IFN-γ mRNA up-regulation in CD4+ over CD8+ T cells was 86% (range, 69-98%). These findings indicated that with DNA immunization, CD4+ T cells were involved only in the induction phase in vitro of IFN-γ responses and that CD8+ T cells are the cells that actually secrete IFN-γ against DR.316. In contrast in RTS,S vaccine-immunized individuals, these results indicate that CD4+ T cells are the effector T cells which produce IFN-γ against the same peptide (DR.316).

Example 6

DNA-Prime/RTS,S Boost Broadens the Repertoire of IFN-γ-Producing T Cells

Figure 3:
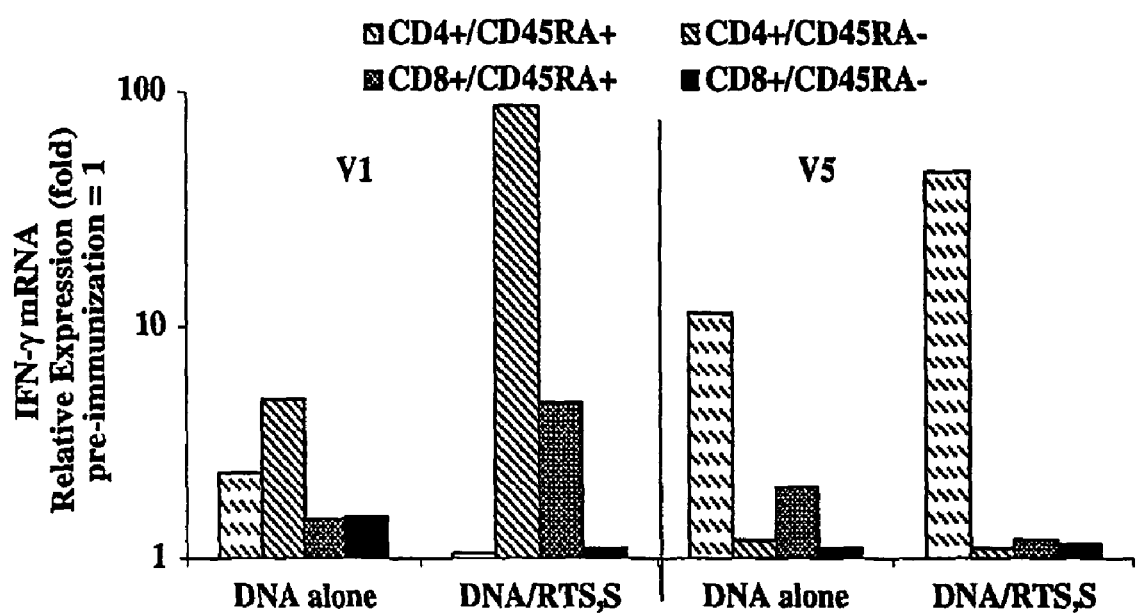
FIG. 3 shows IFN-$\gamma$ mRNA expression levels in T cell subsets measured by real-time PCR IFN-$\gamma$. Frozen cells from two volunteers (V1 and V5) acquired after 3 doses of PfCSP DNA (DNA alone) and after the individuals had been boosted with two doses of RTS,S vaccine (DNA/RTS,S) were studied. Cells were incubated with peptide PfCSP DR.363 for 36 hours, selectively enriched and assessed for IFN-$\gamma$ mRNA expression. After DNA immunization, IFN-$\gamma$ mRNA expression was modestly (5-10 fold) up-regulated in CD4+ T cells in the CD45RA− subset in volunteer V1 and in the CD45RA+ subset in volunteer V5, but not in CD8$^+$ T cells. RTS,S boosting was associated with a significant (80-100 fold) increase in IFN-$\gamma$ mRNA expression levels in the upregulated CD4$^+$ T subset in both volunteers, but not in CD8$^+$ T cells.

The repertoire of IFN-γ-producing T cells recalled was delineated by boosting with the RTS,S vaccine in DNA-primed volunteers. IFN-γ responses to peptide DR.363 (does not contain a CD8+ T cell epitope) were only CD4+ T cell-dependent in volunteers immunized with either the PfCSP DNA vaccine or the RTS,S vaccine alone. The same type of response to DR.363 was detected in 2/3 responders (V1 and V5) in the DNA-primed group after the RTS,S boost. Strikingly, the magnitude of responses measured by IFN-γ mRNA expression levels in CD4+ T cells were increased 94.9 fold in volunteer V1 and 46.7 fold in V5 after the RTS,S boost as compared to a 7.6 fold increase in V1 and 12.5 fold in V5 after the immunization with 3 doses of DNA alone. See "DNA alone" bars in FIG. 3. The magnitude of responses after the RTS,S boost were 12.5 times higher in V1 and 3.7 times higher in V5 than that after the DNA immunization (FIG. 3; compare "DNA alone" bars with "DNA/RTS,S" bars).

IFN-γ responses to peptide DR.316 were dependent upon different T cell subsets in volunteers receiving either the PfCSP DNA vaccine or the RTS,S vaccine alone. DNA-induced responses were both CD4+ T cell and CD8+ T cell-dependent in the induction phase, but only CD8+ T cell-dependent in the effector phase. When measuring the effector phase, T cell populations were depleted after stimulation with peptides. In contrast, RTS,S-induced responses were only CD4+ T cell-dependent in both induction and effector phases. Thus, it was not surprising that the responses to DR.316 in DNA-primed volunteers after the RTS,S boost was a mixture of the two patterns seen in volunteers immunized with either DNA or RTS,S alone (FIG. 2d).

In the induction phase in vitro, both CD4+ and CD8+ T cell-dependent IFN-γ responses to DR.316 were detected in 3/5 responders (4/6 assays) after the first dose of RTS,S. Completely CD4+ T cell-dependent but only partially CD8+ T cell-dependent IFN-γ responses were detected in 4/6 responders (7/12 assays) after the second dose of RTS,S. Depletion of CD8+ T cells did not abrogate IFN-γ production (FIG. 4a), indicating that CD4+ T cells produce IFN-γ as well as CD8+ T cells after the RTS,S boost. Concurrently, in the effector phase, IFN-γ mRNA expression levels were up regulated not only in CD8+ T cells (8/8 responders), but also in CD4+ T cells (4/8 responders after the first dose, 6/8 responders after the second dose of RTS,S), as compared to being up-regulated in only CD8+ T cells in volunteer immunized with DNA alone, or in only CD4+ T cells in volunteers immunized with RTS,S alone (FIG. 2e: DR.316 compare V1 (DNA) to V22 (RTS,S)).

Overall, up-regulation of IFN-γ mRNA in both CD8+ and CD4+ T cells were detected in 6 of the 8 responders, and the up-regulation of IFN-γ mRNA in CD4+ T cells ranged from 3.0 to 28.3 fold (geomean, 6.6 fold) compared with that in CD8+ T cells, which ranged from 4.0 to 281.03 (geomean, 19.7 fold) after the RTS,S boosts. Percentage of IFN-γ mRNA up-regulation in CD4+ over CD8+ T cells was 23.5% (range, 6.5-45.1%). The results here demonstrated that DR316-specific CD4+ T cells in DNA-primed volunteers after the RTS,S boost functioned not only as T helper cells for CD8+ T cell production of IFN-γ (a feature of the DNA-induced IFN-γ response) but also as effectors producing IFN-γ (a feature of the RTS,S-induced IFN-γ response) (Table 5).

The above data demonstrate CD8+ T cell dependent IFN-γ responses in DNA primed-RTS,S boosted volunteers but not in the non-primed volunteers. These data also demonstrate both CD4 and CD8 dependent IFN-γ responses to the same epitopes. Peptide DR.316 was identified to be a CD4 and CD8 overlapping epitope, based on the dependency of IFN-γ responses on different subsets of T cells.

TABLE 4

Comparison of IFN-γ responses in DNA-primed and non-primed groups after the RTS, S immunization

| IFN-γ responses to | specific antigen PfCSP | | backbone antigen HBsAg | |
|---|---|---|---|---|
| HBsAg serology at baseline | HBsAg (+) | HBsAg (−) | HBsAg (+) | HBsAg (−) |
| DNA primed group | | | | |
| after first dose | ++ | ++ | ++ | ++ |
| after second dose | ++ | ++ | ++ | ++ |
| Non-primed group | | | | |
| after first dose | +/− | − | +++ | +++ |
| after second dose | + | ++ | ++++ | ++++ |

Criteria for the score of responsiveness is based on the statistically significant increase (p < 0.05) in terms of (1) the frequency of positive responders, (2) frequency of the positive assays, and (3) the magnitude of positive responses as compared to the baseline, as well as (4) a significant increase in IFN-γ responses after the second immunization compared to after the first immunization. −, no responses; +/−, an increase but not statistically significant; +, ++, +++, and ++++ represent the significantly increase in one, 2, 3, or 4 of the 4 criteria respectively.

Example 7

Antibody Responses in DNA-Primed/RTS,S-Boosted Volunteers

Antibody responses against air-dried *P. falciparum* sporozoites were assessed before immunization with RTS,S, and at 2, 4, 6 and 8 wks after the first and 1, 2, 4 and 6 wks after the second dose of RTS,S. Antibody titers were determined by the indirect fluorescent antibody test (IFAT) as previously described (33). As expected, antibody titers were excellent although there was some variability in the antibody responses among the groups (FIG. 5). Titers peaked 4 weeks after the second dose of RTS,S with geometric mean titers ranging from 5120 to 20480. However, there was no statistically significant difference in antibody titers against whole sporozoites at any time point with one exception. At 2 wks after the first dose, the geometric mean titer of antibodies by IFAT, 3225, in the group of volunteers who had never received PfCSP and had antibodies to HBsAg (DNA−/HB+) was greater than the geometric mean titer, 718.4, in the volunteers who had received PfCSP and had antibodies to HBsAg (DNA+/HB+) (P=0.02). This was primarily due to the high titer, 10240, of a single volunteer in the DNA−/HB+group who withdrew from the study after the 6 wk time point, just prior to the planned second immunization with RTS,S. The statistically significant difference between groups was not present following the second dose of RTS,S.

CONCLUSIONS

The process of developing an effective, sustainable vaccine against infections like *P. falciparum, Mycobacterium tuberculosis*, and HIV has proven to be slower, more difficult and complex than expected. The above analysis of the invention demonstrates that priming with the PfCSP DNA and boosting with RTS,S leads to the induction of responses by both the cellular and humoral arms of the immune system. Furthermore, among individuals with antibodies to HBsAg, those individuals primed with the PfCSP DNA vaccine produced significantly better T cell responses after administration of the RTS,S adjuvanted vaccine than did volunteers who had never received PfCSP DNA. Since most recipients of malaria vaccines, or other vaccines, will have antibodies to HBsAg, either due to immunization or infection, this may provide an important advantage of this prime boost strategy of immunization.

This analysis shows that DNA-primed PfCSP-specific CTL responses were recalled in 50% of the volunteers by boosting with RTS,S 12-14 months after the last vaccination with DNA, indicating that the DNA vaccine was highly effective at the induction of long-lived memory T cell responses. Two of the 5 volunteers with recalled CTL responses after the RTS,S injection had no detectable CTLs after immunization with DNA alone, suggesting that immunization with the DNA vaccine was superior for the induction of memory CTLs in these individuals, but may not have been optimal for induction of effector T cell responses (38, 92). Since there were no CTL responses detected in non-primed volunteers who received RTS,S alone, RTS,S was not capable of priming PfCSP-specific CTLs but had the capacity to boost the CTL responses initiated by the DNA vaccine. DNA-primed PfCSP-specific IFN-γ responses were also boosted strongly by RTS,S, particularly after the first dose. Six of the 10 DNA-primed volunteers had IFN-γ responses against all 4 peptides tested as compared to 2 of 14 non-primed volunteers, who had responses against only one of the 4 peptides. After two doses of RTS,S, although there was no significant difference in terms of the frequency and the magnitude of the responses, the breadth of IFN-γ responses at the epitope level was significantly greater in DNA-primed than in non-primed volunteers. Seven of 8 DNA-primed vs. 3/11 non-primed volunteers responded to at least 2 peptides tested (p=0.0094).

Figure 2:
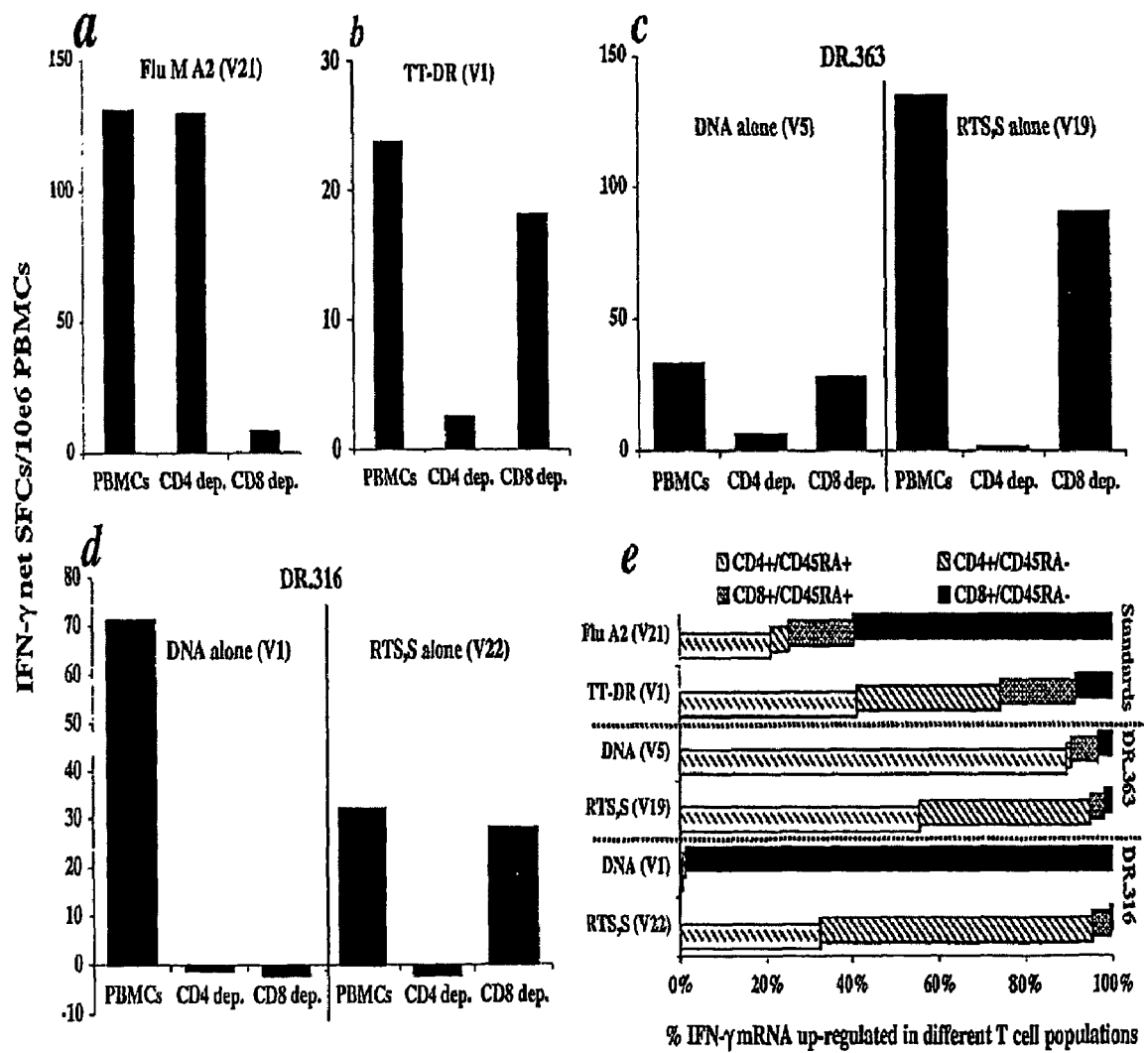
FIG. 2 characterizes the T cells involved in IFN-$\gamma$ responses in vitro in induction and effector phases respectively. ELISPOT assays were conducted with frozen PBMCs from volunteers immunized with 3 doses of PfCSP DNA alone (V1 and V5) or 2 doses of RTS,S alone (V19, V21 and V22), either treated with control Dynabeads or depleted of CD4$^+$ or CD8$^+$ T cells immediately prior to culture with peptides (a) Flu M A2, (b) TT-DR, (c) PfCSP DR.363, or (d) PfCSP DR316. In parallel, IFN-$\gamma$ mRNA expression levels (e) were measured by real-time PCR in selectively enriched T cell populations (CD4$^+$/CD45RA$^+$, CD4$^+$/CD45RA$^-$, CD8$^+$/CD45RA$^+$, and CD8$^+$/CD45RA$^-$) from the same volunteer at the same study time points immediately after 36 hour culture with the same sets of peptides tested in ELISPOT assays.
Figure 4:
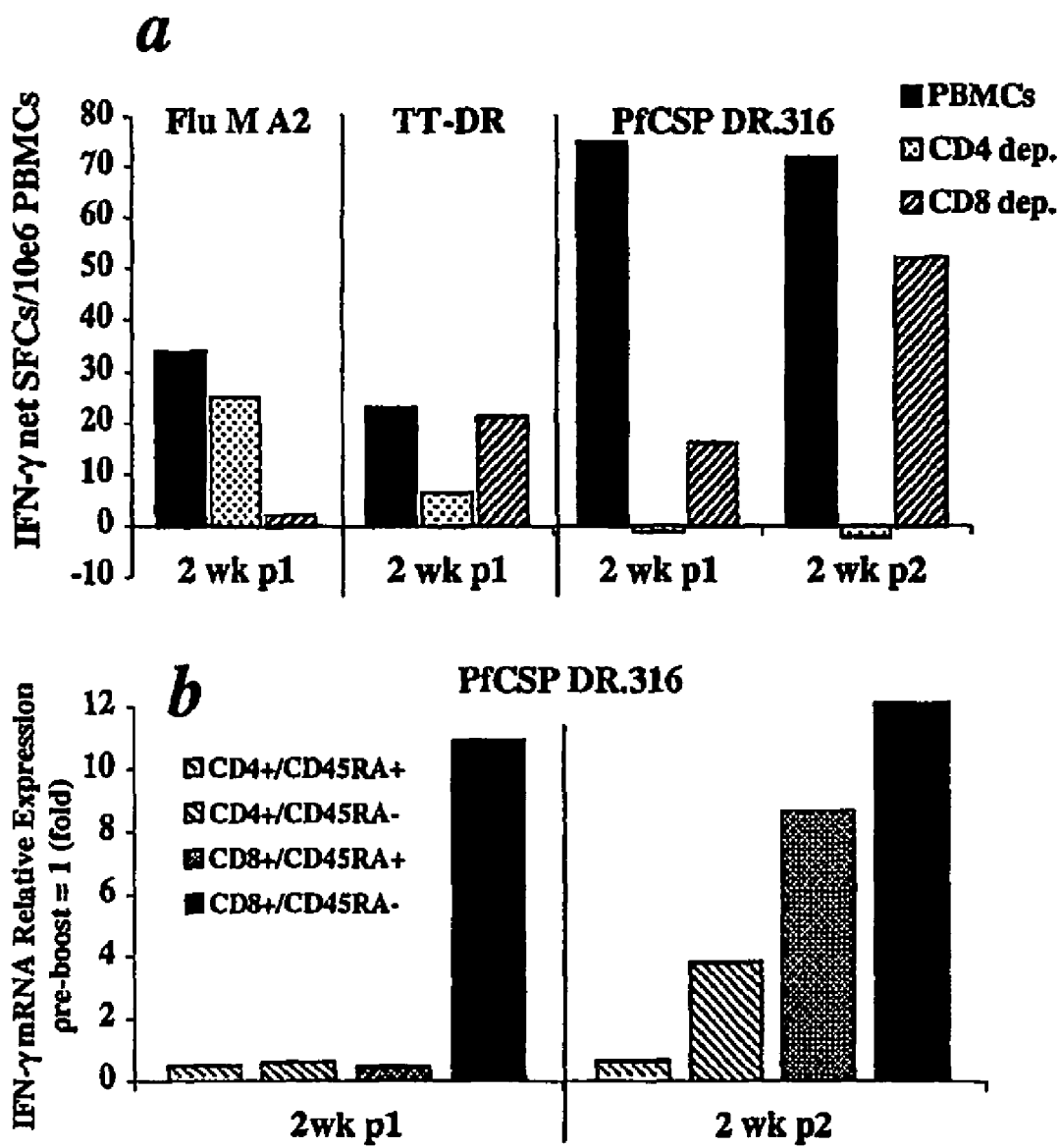
FIG. 4 shows a shift from DNA-induced pattern of IFN-$\gamma$ response to peptide DR316 (CD8$^+$ Tc1 only) after first dose of RTS,S to a mixture of two patterns (CD8$^+$ Tc1 and CD4$^+$ Th1) after administering a second dose of the RTS,S vaccine. In the ex vivo ELISPOT done with cells from volunteer V2, (a)

The results also suggest that DNA-prime/RTS,S boost broadens the repertoire of IFN-γ-producing T cells. DNA priming initiated two profiles of IFN-γ producing T cells: (1) CD4$^+$ T cell-dependent CD8$^+$ type 1 responses against overlapping CD4$^+$/CD8$^+$ T cell epitopes (DR.316 and DR.318), and (2) CD4$^+$ type 1 IFN-γ responses against DR-restricted CD4$^+$ T cell epitopes (DR.363). RTS,S alone, on the other hand, induced only CD4$^+$ type 1 IFN-γ responses (FIG. 2). With regard to DR.316, an overlapping CD4$^+$/CD8$^+$ T cell epitope, DNA alone induced CD4$^+$-dependent CD8$^+$ type 1 responses and RTS,S alone induced CD4$^+$ type 1 responses against this peptide. However, priming with DNA and boosting with RTS,S induced both patterns of IFN-γ responses to DR.316 simultaneously (FIG. 4, Table 4). In addition, RTS,S stimulated CTL responses to new CTL epitopes not detected after DNA priming.

CD4$^+$ T cells may function in a bystander helper capacity for CD8$^+$ T cell production of IFN-γ. The above results confirm this hypothesis by conducting ELISPOT assays and real-time PCR in parallel, in depleted or enriched T cell populations before and after the stimulation of PBMCs with peptide in vitro, respectively. Comparison of the numbers of IFN-γ-producing cells and IFN-γ mRNA expression levels before or after the peptide stimulation delineated the functional profiles of T cells involved in IFN-γ responses induced by either the DNA vaccine and the RTS,S vaccine alone.

The results here suggest that DNA priming may direct post-boost responses to the primed antigen. In regard to immunization with RTS,S, this appears to be of particular importance. RTS,S was designed with HBsAg as a carrier which would enhance T cell responses to the malaria antigen PfCSP. Individuals with antibodies against HBsAg antibodies at baseline had been previously immunized with the hepatitis B vaccine. An anti-malaria vaccine which was delivered in sub-Saharan Africa would be expected to have a target population with significant natural exposure or previous vaccination to HBsAg.

Comparison of the IFN-γ responses to PfCSP between the DNA-primed and non-primed volunteers showed significant differences among those individuals who had existing anti-HBsAg antibodies (Table 1, 3 and 5). Parallel comparison of the IFN-γ responses to HBsAg and PfCSP individually revealed that the RTS,S-induced IFN-γ responses were significantly lower to PfCSP than to HbsAg in all volunteers who were not primed with DNA, and were even lower in individuals with pre-existing anti-HBsAg. Although 13/14 control volunteers responded to HBsAg after one dose of RTS,S, IFN-γ responses to PfCSP were only detected in one of 14 individuals. On the other hand, the responses to the backbone antigen in DNA-primed volunteers had little or no impact on induction of IFN-γ responses to PfCSP, since both the frequency and the magnitude of IFN-γ responses to PfCSP were equivalent between HBsAg sero-positive and sero-negative individuals after the RTS,S boost (Table 5). These results demonstrated that DNA initiates and directs the T cell responses towards the specific antigen, and balances the desired immunity along with the background responses. DNA primed volunteers have comparable IFN-γ responses to both PfCSP and HBsAg regardless of anti-HBsAg seropositivity; non-primed volunteers have significantly stronger IFN-γ responses to HBsAg as compared to PfCSP (Table 4).

There is now considerable effort being directed to producing recombinant fusion proteins and recombinant viruses and bacteria that express the target protein(s). In many cases, for HBsAg, vaccinia, poliovirus, and *Salmonella typhi*, immunized individuals will have pre-existing antibodies against these backbone components of the vaccine. The fact that in individuals with antibodies to the backbone component of the vaccine (e.g. HBsAg), priming with DNA encoding target proteins significantly enhanced the T cell immune responses to these proteins as compared to priming with recombinant protein alone may be an advantage of this prime boost strategy of immunization.

TABLE 5

T cell repertoire of antigen-specific IFN-γ responses

| peptide | DNA alone | RTS, S alone | DNA prime/RTS, S boost |
|---|---|---|---|
| Flu M A2 (CD8+ T epitope) | | | |
| induction phase | CD8+ | CD8+ | CD8+ |
| effector phase | CD8+ | CD8+ | CD8+ |
| TT-DR (CD4+ T epitope) | | | |
| induction phase | CD4+ | CD4+ | CD4+ |
| effector phase | CD4+ | CD4+ | CD4+ |
| PfCSP DR.363 (CD4+ T epitope) | | | |
| induction phase | CD4+ | CD4+ | CD4+ |
| effector phase | CD4+ | CD4+ | CD4+ |
| PfCSP DR.316 (overlapping CD4+ and CD8+ T epitope) | | | |
| induction phase | CD4+ and CD8+ | CD4+ | CD4+ and CD8+ |
| effector phase | CD8+ | CD4+ | CD8+ and CD4+ |

Priming of immune responses using DNA as the vaccine vehicle allows for focusing of the initial T cell responses on the recombinant immunogen, simply because that is the only foreign protein expressed in a DNA vaccine. Although recombinant RTS,S or poxviruses may be intrinsically more immunogenic than DNA vectors as vaccine vehicles, virus-infected cells produce a large number of virus-derived epitopes that compete with the recombinant immunogen for T cell immunodominance. Many individuals receiving a vaccine will most likely have been naturally exposed to the carrier antigens, or have received other vaccinations containing the antigen in a recombinant virus or protein, so that effector responses against the carrier antigens will interfere with the induction of T cell responses to specific antigens.

In this study, antigen-specific CD4+ helper, CD8+ T cell-dependent CTL and IFN-γ responses, and Th1-type CD4+ T cell-dependent IFN-γ responses were all simultaneously achieved in human volunteers by a DNA priming/recombinant protein boosting immunization strategy. This strategy, capable of inducing both arms of the immune response, offers unique advantages for preventive and therapeutic vaccines.

The following publications, as well as those mentioned anywhere else in this application, are hereby specifically incorporated by reference:

1. Aguiar J C, Hedstrom R C, Rogers W O, Charoenvit Y, Sacci J B Jr, Lanar D E, Majam V F, Stout R R, and Hoffman S L. Enhancement of the immune response in rabbits to a malaria DNA vaccine by immunization with a needle-free jet device. *Vaccine* 20:275-80 (2001).
2. Aidoo, M., Lalvani, A., Allsopp, C. E., Plebanski, M., Meisner, S. J., Krausa, P., Browning, M., Morris Jones, S., Gotch, F., Fidock, D. A. and et al, Identification of conserved antigenic components for a cytotoxic T lymphocyte-inducing vaccine against malaria. *Lancet* 345:1003 (1995).
3. al Yaman, F., Genton, B., Anders, R., Falk M, Triglia T, Lewis, D. et al. Relationship between humoral response to *Plasmodium falciparum* merozoite surface antigen-2 and malaria morbidity in a highly endemic area of Papua New Guinea. *Am. J. Trop. Med. Hyg.* 51:593 (1994).
4. al Yaman, F., Genton, B., Anders R, Taraika J, Ginny M, Mellor S et al. Assessment of the role of the humoral response to *Plasmodium falciparum* MSP2 compared to RESA and SPf66 in protecting Papua New Guinean children from clinical malaria. Parsite Immunol 17:493 (1995).
5. Anders R F, Crewther P E, Edwards S, Margetts M, Matthew M L, Pollock B, Pye D. Immunisation with recombinant AMA-1 protects mice against infection with *Plasmodium chabaudi*. *Vaccine* 16(2-3):240-7 (1998).
6. Barouch, D. H. et al. Control of viremia and prevention of clinical AIDS in rhesus monkeys by cytokine-augmented DNA vaccination. *Science* 290, 486-92. (2000).
7. Blackman, M. J., Heidrich, H. G., Donachie, S., McBride, J. S. and Holder, A. A. A single fragment of a malaria merozoite surface protein remains on the parasite during red cell invasion and is the target of invasion-inhibiting antibodies. *J. Exp. Med.* 172:379 (1990).
8. Bojang K A, Milligan P J, Pinder M, Vigneron L, Alloueche A, Kester K E, Ballou W R, Conway D J, Reece W H, Gothard P, Yamuah L, Delchambre M, Voss G, Greenwood B M, Hill A, McAdam K P, Tomieporth N, Cohen J D, Doherty T; RTS,S Malaria Vaccine Trial Team. Efficacy of RTS,S/AS02 malaria vaccine against *Plasmodium falciparum* infection in semi-immune adult men in The Gambia: a randomised trial. *Lancet* 358:1927-34 (2001).
9. Brazolot Millan C L, Weeratna R, Krieg A M, Siegrist C A, Davis H L. CpG DNA can induce strong Th1 humoral and cell-mediated immune responses against hepatitis B surface antigen in young mice. *Proc Natl Acad Sci USA.* 95:15553-8 (1998).
10. Burns, J. M., Daly, T. M., Vaidya, A. B. and Long, C. A. The 3' portion of the gene for a *Plasmodium yoelii* merozoite surface antigen encodes the epitope recognized by a protective monoclonal antibody. *Proc. Natl. Acad. Sci. USA* 5:602 (1988).

11. Calarota, S. et al. Cellular cytotoxic response induced by DNA vaccination in HIV-1-infected patients. *Lancet* 351: 1320-25 (1998).
12. Chang, S. P., Case, S. E., Gosnell, W. L., Hashimoto, A., Kramer, K. J., Tam, L. Q., Hashiro, C. Q., Nikaido, C. M., Gibson, H. L., Lee Ng, C. T., Barr, P. J., Yokota, B. T. and Hut, G. S. A recombinant baculovirus 42-kilodalton C-terminal fragment of *Plasmodium falciparum* merozoite surface protein 1 protects *Aotus* monkeys against malaria. *Infect. Immun.* 64:253 (1996).
13. Charoenvit, Y., Leef, M. L., Yuan, L. F., Sedegah, M. and Beaudoin, R. L. Characterization of *Plasmodium yoelii* monoclonal antibodies directed against stage-specific sporozoite antigens. *Infect Immun.* 55:604 (1987).
14. Charoenvit, Y., Collins, W. E., Jones, T. R., Millet, P., Yuan, L., Campbell, G. H., Beaudoin, R. L., Broderson, J. R. and Hoffman, S. L. Inability of malaria vaccine to induce antibodies to a protective epitope within its sequence. *Science* 251:668 (1991).
15. Charoenvit, Y., Mellouk, S., Cole, C., Bechara R., et al. *Plasmodium yoelii:* 17-kD hepatic and erythrocytic stage protein is the target of an inhibitory monoclonal antibody. *Exp Parasitol.* 80:419-429 (1995).
16. Charoenvit, Y., Fallarme Majam, V., Corradin, G. P., et al. CD4+ T-cell- and gamma interferon dependent protection against murine malaria by immunization with linear synthetic peptide from *Plasmodium yoelii* 17-kilodaldon hepatocyte erythrocyte protein. *Infect. Immun.* 67:5604-5614 (1999).
17. Clark, J. T, Donachi S., Anand R. et al. 46-53 kD glycoprotein from the surface of *Plasmodium falciparum* merozoites. *Mol Biochem.* 32:15-24 (1988).
18. Collins, W. E., Galland, G. G., Sullivan, J. S. and Morris, C. L. Selection of different strains of *Plasmodium falciparum* for testing blood-stage vaccines in *Aotus nancymai* monkeys. *Am. J. Trop. Med. Hyg.* 51:224-232 (1994).
19. Collins, W. E., Pye, D., Crewther, P. E., Vandenberg, K. L., Galland, G. G., Sulzer, A. J., Kemp, D. J., Edwards, S. J., Coppel, R. L., Sullivan, J. S., Morris, C. L. and Anders, R. F. Protective immunity induced in squirrel monkeys with recombinant apical membrane antigen-1 of *Plasmodium fragile*. *Am. J. Trop. Med. Hyg.* 51:711-719 (1994).
20. Daly, T. M. and Long, C. A. A recombinant 15-kilodalton carboxyl-terminal fragment of *Plasmodium yoelii yoelii* 17XL merozoite surface protein 1 induces a protective immune response in mice. *Infect. Immun.* 61:2462-2467 (1993).
21. Dame J B, Williams J L, McCutchan T F, Weber J L, Wirtz R A, Hockmeyer W T, Maloy W L, Haynes J D, Schneider I, Roberts D, et al. Structure of the gene encoding the immunodominant surface antigen on the sporozoite of the human malaria parasite *Plasmodium falciparum. Science* 225(4662):593-9 (1984).
22. Daubersies P, Thomas A W, Millet P, Brahimi K, Langermans J A, Ollomo B, BenMohamed L, Slierendregt B, Eling W, Van Belkum A, Dubreuil G, Meis J F, Guerin-Marchand C, Cayphas S, Cohen J, Gras-Masse H, Druilhe P, and Mohamed L B. Protection against *Plasmodium falciparum* malaria in chimpanzees by immunization with the conserved pre-erythrocytic liver-stage antigen 3. *Nat Med.* 6:1258-63 (2000).
23. Davis H L, Weeratna R, Waldschmidt T J, Tygrett L, Schorr J, Krieg A M, Weeranta R. CpG DNA is a potent enhancer of specific immunity in mice immunized with recombinant hepatitis B surface antigen. *J Immunol.* 160: 870-6 (1998).
24. Deans, J. A. Protective antigens of bloodstage *Plasmodium knowlesi* parasites. *Plilos. Trans. R. Soc. Lond. Biol.* 307:159-169 (1984).
25. Deans, J. A., Knight, A. M., Jean, W. C., Waters, A. P., Cohen, S. and Mitchell, G. H. Vaccination trials in rhesus monkeys with a minor, invariant, *Plasmodium knowlesi* 66 kD merozoite antigen. *Parasite Immunol.* 10:535-552 (1988).
26. Delplace P, Bhatia A, Cagnard M et al. Protein p126: a parasitophorous vacuole antigen associated with the release of *Plasmodium falciparum* merozoites. *Biol Cell* 64:215 (1987).
27. Doolan, D. L., Sedegah, M., Hedstrom, R. C., Hobart, P., Charoenvit, Y. and Hoffman, S. L. Circumventing genetic restriction of protection against malaria with multi-gene DNA immunization: CD8+ T cell, interferon-gamma, and nitric oxide dependent immunity. *J. Exp. Med.* 183:1739-1746 (1996).
28. Doolan, D. L., Hedstrom, R. C., Rogers, W. O., Charoenvit, Y., Rogers, M., De la Vega, P. and Hoffman, S. L. Identification and characterization of the protective hepatocyte erythrocyte protein 17 kDa gene of *Plasmodium yoelii*, homolog of *Plasmodium falciparum* exported protein 1. *J. Biol. Chem.* 271:17861-17868 (1996).
29. Doolan, D. L, Hoffman, S. L., Southwood, S., Wentworth, P. A., Sidney, J., Chestnut, R. W., Keogh, E., Apella, E., Nutman, T. B., Lal, A. A., Gordon, D. M., Oloo, A. and Sette, A. Degenerate cytotoxic T cell epitopes from *P. falciparum* restricted by HLA-A and HLA-B supertypes alleles. *Immunity* 7:97-112 (1997).
30. Doolan D L, Hedstrom R C, Gardner M J, Sedegah M, Wang H, Gramzinski R A, Margalith M, Hobart P, and Hoffman S L. DNA vaccination as an approach to malaria control: current status and strategies. *Curr Topic Microbiol Immunol* 226:37-56 (1998).
31. Doolan D L, Hoffman S L. IL-12 and NK cells are required for antigen-specific adaptive immunity against malaria initiated by CD8+ T cells in the *Plasmodium yoelii* model. *J Immunol* 163(2):884-92 (1999).
32. Egan, J. E., Weber, J. L., Ballou, W. R., Hollingdale, M. R., Majarian, W. R., Gordon, D. M., Maloy, W. L., Hoffman, S. L., Wirtz, R. A., Schneider, I., Woollett, G. R., Young, J. F. and Hockmeyer, W. T. Efficacy of murine malaria sporozoite vaccines: implications for human vaccine development. *Science* 236:453-456 (1987).
33. Epstein J, Gorak E, Y Charoenvit, R Wang, N Freydberg, O Osinowo, T L Richie, E Stoltz, F Trespalacios, J Nerges, J Ng, V Fallarme-Majam, E Abot, L Goh, S Parker, S Kumar, R Hedstrom, J Norman, R Stout, S L Hoffman. Safety, Tolerability and Lack of Antibody Responses following Administration of a PfCSP DNA Malaria Vaccine via Needle or Needle-free Jet Injection, and Comparison of Intramuscular and Combination Intramuscular/Intradermal Routes. *Human Gene Therapy* 13:1551-60 (2002).
34. Etlinger, H. M., Caspers, P., Matile, H., Schoenfeld, H. J., Stueber, D. and Takacs, B. Ability of recombinant or native proteins to protect monkeys against heterologous challenge with *Plasmodium falciparium*. *Infect. Immun.* 59:3498-3503 (1991).
35. Freeman, R. R. and Holder, A. A. Characteristics of the protective response of BALB/c mice immunized with a purified *Plasmodium yoelii* schizont antigen. *Clin. Exp. Immunol.* 54:609-616 (1983).
36. Gordon D M, McGovern T W, Krzych U, Cohen J C, Schneider I, LaChance R, Heppner D G, Yuan G, Hollingdale M, Slaoui M, et al. Safety, immunogenicity, and efficacy of a recombinantly produced *Plasmodium*

*falciparum* circumsporozoite protein-hepatitis B surface antigen subunit vaccine. *J Infect Dis* 171:1576-85 (1995).
37. Gramzinski R A, Maris D C, Doolan D, Charoenvit Y, Obaldia N, Rossan R, Sedegah M, Wang R, Hobart P, Margalith M, and Hoffman S. Malaria DNA vaccines in *Aotus* monkeys. *Vaccine* 15:913-915 (1997).
38. Gurunathan, S., Wu, C. Y., Preidag, B. L. & Seder, R. A. DNA vaccines: a key for inducing long-term cellular immunity. *Curr Opin Immunol* 12, 442-7 (2000).
39. Harnyuttanakorn P, McBride J S, Donachie S, Heidrich H G, Ridley R G. Inhibitory monoclonal antibodies recognise epitopes adjacent to a proteolytic cleavage site on the RAP-1 protein of *Plasmodium falciparum*. *Mol Biochem Parasitol*. 55:177-86 (1992).
40. Hedstrom R, Doolan D, Wang R, et al. In vitro expression and in vivo immunogenicity of *Plasmodium falciparum* pre-erythrocytic stage DNA vaccines. *Int J Molec Med* 2:29-38 (1998).
41. Herrington, D., Davis, J., Nardin, E., Beier, M., Cortese, J., Eddy, H., Losonsky, G., Hollingdale, M., Sztein, M., Levine, M., Nussenzweig, R. S., Clyde, D. and Edelman, R. Successful immunization of humans with irradiated sporozoites: humoral and cellular responses of the protected individuals. *Am. J. Trop. Med. Hyg.* 45:539-547 (1991).
42. Hilgers L A, Snippe H, Jansze M, Willers J M. Synergistic effects of synthetic adjuvants on the humoral immune response. *Int Arch Allergy Appl Immunol*. 79:392-6 (1986).
43. Hilgers L A, Snippe H, Jansze M, Willers J M. Synthetic sulpholipopolysaccharides: novel adjuvants for humoral immuneresponses. *Immunology*. 60:141-6 (1987).
44. Hill A V S, Elvin J, Willis A C et al. Molecular analysis of the association of HLA-B53 and resistance to severe malaria. *Nature* 360:434 (1992).
45. Hoffman, S. L. and Doolan, D. L. Malaria vaccines-targeting infected hepatocytes. *Nature Med.* 6:1218-19 (2000).
46. Holder, A. A. and Freeman, R. R. Immunization against blood-stage rodent malaria using purified parasite antigens. *Nature* 294:361-364 (1981).
47. Horn N A, Meek J A, Budahazie G, Marquet M. Cancer Gene Therapy using plasmid DNA: purification of DNA for human clinical trials. *Human Gene Therapy* 6(5): 565-73 (1995).
48. Inselburg, J., Bzik, D. J., Li, W. B., Green, K. M., Kansopon, J., Hahm, B. K., Bathurst, I. C., Barr, P. J. and Rossan, R. N. Protective immunity induced in *Aotus* monkeys by recombinant SERA proteins of *Plasmodium falciparum*. *Infect. Immun.* 59:1247-1250 (1991).
49. Inselburg, J., Bathurst, I. C., Kansopon, J., Barchfeld, G. L., Barr, P. J. and Rossan, R. N. Protective immunity induced in *Aotus* monkeys by a recombinant SERA protein of *Plasmodium falciparum*: adjuvant effects on induction of protective immunity. *Infect. Immun.* 61:2041-2047 (1993).
50. Kedzierski L, Black C G, and Coppel R L. Immunization with recombinant *Plasmodium yoelii* merozoite surface protein 4/5 protects mice against lethal challenge. *Infect Immun.* 68:6034-7 (2000).
51. Kensil C R, Patel U, Lennick M, Marciani D. Separation and characterization of saponins with adjuvant activity from Quillajasaponaria Molina cortex. *J Immunol.* 146: 431-7 (1991).
52. Kensil, C. R Saponins as vaccine adjuvants. *Crit Rev Ther Drug Carrier Syst,* 12:1-55 (1996).
53. Kester K. E., McKinney D. A., Tomieporth N, Ockenhouse C. F., Heppner D. G., Hall T., Krzych U., Delchambre M, Voss G, Dowler M G, Palensky J, Wittes J, Cohen J, Ballou W R; RTS,S Malaria Vaccine Evaluation Group. Efficacy of Recombinant Circumsporozoite Protein Vaccine Regimens Against Experimental *Plasmodium falciparum* Malaria *J Infect Dis* 183(4):640-7 (2001).
54. Kester, K. E. et al. Efficacy of recombinant circumsporozoite protein vaccine regimens against experimental *Plasmodium falciparum* malaria. *J. Infect. Dis.* 183:64047 (2001).
55. Khusmith, S., Charoenvit, Y., Kumar, S., Sedegah, M., Beaudoin, R. L. and Hoffman, S. L. Protection against malaria by vaccination with sporozoite surface protein 2 plus CS protein. *Science* 252:715-718 (1991).
56. Khusmith, S., Sedegah, M. and Hoffman, S. L. Complete protection against *Plasmodium yoelii* by adoptive transfer of a CD8+ cytotoxic T cell clone recognizing sporozoite surface protein 2. *Infect Immun.* 62:2979-2983 (1994).
57. Krieg A M, Yi A K, Matson S, Waldschmidt T J, Bishop G A, Teasdale R, Koretzky G A, Klinman D M. CpG motifs in bacterial DNA trigger direct B-cell activation. *Nature.* 374: 546-9 (1995).
58. Kumar, S., Yadava, A., Keister, D. B., Tian, J. H., Ohl, M., Perdue Greenfield, K. A., Miller, L. H. and Kaslow, D.C. Immunogenicity and in vivo efficacy of recombinant *Plasmodium falciparum* merozoite surface protein-1 in *Aotus* monkeys. *Mol. Med.* 1:325-332 (1995).
59. Kumar S, Collins W, Egan A, Yadava A, Garraud O, Blackman M J, Patino J A, Diggs C, Kaslow D C. Immunogenicity and Efficacy in *Aotus* Monkeys of Four Recombinant *Plasmodium falciparum* Vaccines in Multiple Adjuvant Formulations Based on the 19-Kilodalton C Terminus of Merozoite Surface Protein 1. *Infect Immun* 68:2215-2223 (2000).
60. Lacaille-Dubois, M and Wagner H. A review of the biological and pharmacological activities of saponins. *Phytomedicine* 2:363-386 (1996).
61. Lalvani A, Moris P, Voss G, Pathan A, et al. Potent induction of focused Th1-Type cellular and humoral immune responses by RTS,S/SBAS2, a recombinant *Plasmodium falciparum* malaria vaccine. *J Infect Dis* 180:1656-64 (1999).
62. Le T, Coonan K, Hedstrom R, et al. Safety, tolerability, and humoral immune responses after intramuscular administration of a malaria DNA vaccine to healthy adult volunteers. *Vaccine* 18:1893-1901 (2000).
63. Lee, A. Y. et al. Quantification of the number of cytotoxic T cells specific for an immunodominant HCV-specific CTL epitope primed by DNA immunization. *Vaccine* 18:1962-68 (2000).
64. Luke C J, Carner K, Liang X, Barbour A G. An ospA-based DNA vaccine protects mice against infection with *Borrelia burgdorferi*. *J Inf Dis* 175:191-7 (1997).
65. Majarian W R, Daly T M et al. Passive immunization against murine malaria with an IgG3 monocloncal antibody. *J Immunol* 132: 3131 (1984).
66. Malik, A., Egan, J. E., Houghten, R. A., Sadoff, J. C. and Hoffman, S. L. Human cytotoxic T lymphocytes against the *Plasmodium falciparum* circumsporozoite protein. *Proc. Natl. Acad. Sci. USA* 88:3300-3304 (1991).
67. Martin T, Parker S E, Hedstrom R, et al. Plasmid DNA malaria vaccine: the potential for genomic integration following intramuscular injection. *Human Gen Ther* 10:759-68 (1999).
68. McCluskie M J, Davis H L. CpG DNA is a potent enhancer of systemic and mucosal immune responses against hepatitis B surface antigen with intranasal administration to mice. *J Immunol.* 161:4463-6 (1998).

69. Moreno, A., Clavijo, P., Edelman, R., Davis, J., Sztein, M., Herrington, D. and Nardin, E. Cytotoxic CD4+ T cells from a sporozoite-immunized volunteer recognize the *Plasmodium falciparum* CS protein. *Int. Immunol.* 3:997-1003 (1991).
70. Mosmann, T. R. and Coffman, R. L. TH1 and TH2 cells: different patterns of lymphokine secretion lead to different functional properties. *Ann. Rev. of Immunol.* 7:145-173 (1989).
71. Musti, A. M., Zehner, Z., Bostian, K. A., Paterson, B. M., and Kramer, R. A. Transcriptional mapping of two yeast genes coding for glyceraldehyde 3-phosphate dehydrogenase isolated by sequence homology with the chicken gene. *Gene* 25:133-143 (1983).
72. Oeuvray C, Bouharoun Tayoun H, Gras Masse H et al. Merozoite surface protein-3:a malaria protein inducing antibodies that promote *Plasmodium falciparum* killing by cooperation with blood monocytes. *Blood* 84:1594 (1994).
73. Oeuvray C, Bouharoun Tayoun H, Gras Masse H et al. A novel merozoite surface antigen of *Plasmodium falciparum* (MSP-3), identified by cellular-antibody cooperative mechanism antigenicity and biological activity of antibodies. *Mem Inst Oswaldo Cruz* Supp 2:77 (1994).
74. Panina-Bordignon P, Tan A, Termijtelen A, Demotz S, Corradin G, Lanzavecchia A. Universally immunogenic T cell epitopes: promiscuous binding to human MHC class II and promiscuous recognition by T cells. *Eur J Immunol* 12:223742 (1989).
75. Parker S E, Borellini F, Wenk M L, et al. Plasmid DNA malaria vaccine: tissue distribution and safety studies in mice and rabbits. *Human Gene Ther* 10(5):741-58 (1999).
76. Perrin, L. H., Dayal, R. and Rieder, H. Characterization of antigens from erythrocytic stages of *Plasmodium falciparum* reacting with human immune sera. *Trans. R. Soc. Trop. Med. Hyg.* 75:163-165 (1981).
77. Perrin, L. H., Ramirez, E., Lambert, P. H. and Miescher, P. A. Inhibition of *P. falciparum* growth in human erythrocytes by monoclonal antibodies. *Nature* 289:301-303 (1981).
78. Potocnjak, P., Yoshida, N., Nussenzweig, R. S. and Nussenzweig, V. Monovalent fragments (Fab) of monoclonal antibodies to a sporozoite surface antigen (Pb44) protect mice against malaria infection. *J. Exp. Med.* 151:1504-1513 (1980).
79. Proteins—Structure and Molecular Properties, 2nd Ed., T. E. Creighton, W. H. Freeman and Company, New York, 1993.
80. Ramasamy R. Studies on glycoproteins in the human malaria parasite *Plasmodium falciparum*-lectin binding properties and the possible carbohydrate-protein linkage. *Immunol Cell Biol* 65: 147 (1987).
81. Ramasamy R J, Jones G, Lord R. Characterization of an inhibitory monocloncal antibody defined epitope on a malaria vaccine candidate antigen. *Immunol Lett* 23:305 (1990).
82. Rattan et al. Protein Synthesis: Post-translational Modifications and Aging. *Ann NY Acad Sci* 663:48-62 (1992).
83. *Remington's Pharmaceutical Sciences,* 18th Edition (A. Gennaro, ed., Mack Pub., Easton, Pa., 1990).
84. Ridley R G, Takacs B, Etlinger H, Scaife J G. A rhoptry antigen of *Plasmodium falciparum* is protective in Saimiri monkeys. *Parasitology* 101:187-92 (1990).
85. Rodrigues, M. M., Cordey, A.-S., Arreaza, G., Corradin, G., Romero, P., Maryanski, J. L., Nussenzweig, R. S. and Zavala, F. CD8+ cytolytic T cell clones derived against the *Plasmodium yoelii* circumsporozoite protein protect against malaria. *Int. Immunol.* 3:579-585 (1991).
86. Rogers, W. O. et al. Multistage multiantigen heterologous prime boost vaccine for *Plasmodium* knowlesi malaria provides partial protection in rhesus macaques. *Infect Immun* 69:5565-72 (2001).
87. Romero, P., Maryanski, J. L., Corradin, G., Nussenzweig, R. S., Nussenzweig, V. and Zavala F. Cloned cytotoxic T cells recognize an epitope in the circumsporozoite protein and protect against malaria. *Nature* 341:323-325 (1989).
88. Saul A, Lord R, Jones G L et al. Protective immunization with invariant peptides of the *Plasmodium falciparum* antigen MSA2. *J Immunol* 148:208 (1992).
89. Schofield L, Bushell G R, Cooper J A et al. A rhoptry antigen of *Plasmodium falciparum* contains conserved and variable epitopes recognised by inhibitory monoclonal antibodies. *Mol Biochem Parasitol.* 18:183-95 (1986).
90. Schofield L, Villaquiran J, Ferreira A, eta 1. Gamma-interferon, CD8+ T cells and antibodies required for immunity to malaria sporozoites. *Nature.* 330:664-666 (1987).
91. Sedegah, M. et al. Improving protective immunity induced by DNA-based immunization: priming with antigen and GM-CSF-encoding plasmid DNA and boosting with antigen-expressing recombinant poxvirus. *J Immunol* 164:5905-12 (2000).
92. Seder, R. A. & Hill, A. V. Vaccines against intracellular infections requiring cellular immunity. *Nature* 406, 793-8. (2000).
93. Seguin M C, Klotz F W, Schneider I, Weir J P, Goodbary M, Slayter M, et al. Induction of nitric oxide synthase protects against malaria in mice exposed to irradiated *Plasmodium berghei* infected mosquitoes: involvement of interferon gamma and CD8+ T cells. *J Exp Med* 180:353-358(1994).
94. Seifter et al. Analysis for protein modifications and non-protein cofactors. *Meth Enzymol* 182:626-646 (1990).
95. Shi, Y. P., Sayed, U., Qari, S. H., Roberts, J. M., Udhayakumar, V., Oloo, A. J., Hawley, W. A., Kaslow, D. C., Nahlen, B. L. and Lal, A. A. Natural immune response to the C-terminal 19-kilodalton domain of *Plasmodium falciparum* merozoite surface protein 1. *Infect. Immun.* 64:2716-2723 (1996).
96. Siddiqui, W. A., Tam, L. Q., Kramer, K. J., Hui, G. S., Case, S. E., Yamaga, K. M., Chang, S. P., Chan, E. B. and Kan, S. C. Merozoite surface coat precursor protein completely protects *Aotus* monkeys against *Plasmodium falciparum* malaria. *Proc. Natl. Acad. Sci. USA* 84:3014-3018 (1987).
97. Sim B K L, Orlandi P A, Haynes J D et al. Primary structure of the 175K *Plasmodium falciparum* erythrocyte binding antigen and identification of a peptide which eleicits antibodies that inhibit malaria merozoite invasion. *J Cell Biol* III: 1877 (1990).
98. Sim B K L, Chitnis C E, Deal C D et al. *Plasmodium falcipaum*: further characterization of a functionally active region of the merozoite ligand EBA-175 78: 259 (1994).
99. Stoute J A, Slaoui M, Heppner D G et al. A preliminary evaluation of a recombinant circumsporozoite protein vaccine against *Plasmodium falciparum* malaria N *Eng J Med* 336: 86-91 (1997).
100. Stoute J A, Kester K E, Krzych U, et al. Long-term efficacy and immune responses following immunization with the RTS,S malaria vaccine. *J Infect Dis* 178: 1139-44 (1998).
101. Thomas A W, Trape J F, Rogier C, Goncalves A, Rosario V E, Narum D L. High prevalence of natural antibodies against *Plasmodium falciparum* 83-kilodalton apical membrane antigen (PF83/AMA-1) as detected by captureenzyme-linked immunosorbent assay using full-length baculovirus recombinant PF83/AMA-1. *Am J Trop Med Hyg* 51:730-40 (1994).

102. Thomas A W, Narum D, Waters A P, Trape J F, Rogier C, Goncalves A, Rosario V, Druilhe P, Mitchell G H, Dennis D. Aspects of immunity for the AMA-1 family of molecules in humans and non-human primates malarias. *Mem Inst Oswaldo Cruz* 89 Suppl 2:67-70 (1994).

103. Valenzuela, P., Gray, P., Quiroga, M., et al., Nucleotide Sequences of the Gene Coding for the Major Protein of Hepatitis B Virus Surface Antigen. *Nature* 280:815-819 (1979).

104. Wang, R., Charoenvit, Y., Corradin, G., De la Vega, P., Franke, E. D. and Hoffman, S. L. Protection against malaria by *Plasmodium yoelii* sporozoite surface protein 2 linear peptide induction of CD4+ T cell- and IFN-gamma-dependent elimination of infected hepatocytes. *J. Immunol.* 157:4061-4067 (1996).

105. Wang, R., Doolan, D. L., Le, T. P., Hedstrom, R. C., Coonan, K. M., Charoenvit, Y., Jones, T. R., Hobart, P., Margalith, M., Ng, J., Weiss, W. R., Sedegah, M., de Taisne, C., Norman, J. A. and Hoffman, S. L. Induction of antigen-specific cytotoxic T lymphocytes in humans by a malaria DNA vaccine. *Science* 282:476-480 (1998).

106. Wang R, Doolan D L, Charoenvit Y, Hedstrom R C, Gardner M J, Hobart P, Tine J, Sedegah M, Fallarme V, Sacci J B Jr, Kaur M, Klinman D M, Hoffman S L, Weiss W R. Simultaneous induction of multiple antigen-specific cytotoxic T lymphocytes in nonhuman primates by immunization with a mixture of four *Plasmodium falciparum* DNA plasmids. *Infect Immun* 66:4193-202 (1998).

107. Wang R, Epstein J, Baraceros F M, Gorak E J, Charoenvit Y, Carucci D J, Hedstrom R C, Rahardjo N, Gay T, Hobart P, Stout R, Jones T R, Richie T L, Parker S E, Doolan D L, Norman J, Hoffman S L. Induction of CD4[(+)] T cell-dependent CD8(+) type 1 responses in humans by a malaria DNA vaccine. *PNAS-USA* 98(19):10817-22 (2001).

108. Weiss W R, Sedegah M, Beaudoin R L, Miller L H, Good M F. CD8+ T cells (cytotoxic/suppressors) are required for protection in mice immunized with malaria sporozoites. *PNAS-USA.* 85(2):573-6 (1988).

109. Weiss W R, Berzofsky J A, Houghten R A, Sedegah M, Hollindale M, Hoffman S L. A T cell clone directed at the circumsporozoite protein which protects mice against both *Plasmodium yoelii* and *Plasmodium berghei. J Immunol* 15; 149(6):2103-9 (1992).

110. WHO Report. State of the World's Vaccines and Immunization. Geneva: World Health Organization. (1996).

111. Wizel, B., Rogers, W. O., Houghten, R. A., Lanar, D. E., Tine, J. A. and Hoffman, S. L. Induction of murine cytotoxic T lymphocytes against *Plasmodium falciparum* sporozoite surface protein 2. *Eur. J. Immunol.* 24:1487-1495 (1994).

112. Wizel, B., Houghten, R., Church, P., Tine, J. A., Lanar, D. E., Gordon, D. M., Ballou, W. R., Sette, A. and Hoffman, S. L. HLA-A2-restricted cytotoxic T lymphocyte responses to multiple *Plasmodium falciparum* sporozoite surface protein 2 epitopes in sporozoite-immunized volunteers. *J. Immunol.* 155:766-775 (1995).

113. Wold, F., Post-translational Protein Modifications: Perspectives and Prospects, 1-12, in Post-translational Covalent Modification of Proteins, B. C. Johnson, Ed., Academic Press, New York, 1983.

114. Yang C, Collins W E, Sullivan J S et al. Partial protection against *Plasmodium vivax* blood-stage infection in Saimiri monkeys by immunization with a recombinant C-terminal fragment of merozoite surface protein 1 in block copolymer adjuvant. *Infect Imm* 67: 342 (1999).

115. Zinsser Microbiology 1180-83 (Wolfgang K Joklik, Hilda P. Willett, D. Bernard Amos, and Catherine M. Wilfert eds., 20th ed, Appleton and Lange 1992).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for eliciting an immune response against a malaria-causing pathogen in a human, the method comprising:
   a) priming an immune response in a human by administering a priming composition comprising at least one polynucleotide encoding all or substantially all of the circumsporozoite protein in a priming dose effective to establish the response; and
   b) boosting the primed immune response in the human by subsequently administering a boosting composition comprising at least one polypeptide which comprises substantially all of the circumsporozoite protein or a fragment thereof in a boosting dose effective to boost the primed immune response
   wherein administration of the priming composition primes CD8+ T cells and administration of the boosting composition recalls the primed CD8+ T cells, broadens the primed CD8+ T cell response, and results in the generation of anti-malaria CD8+ T cells, anti-malaria CD4+ T cells, and anti-malaria antibodies.

2. The method of claim 1, wherein the boosting composition comprises all or part of the priming composition.

3. The method of claim 1, wherein the priming dose is between 0.01 µg and 50 mg.

4. The method of claim 3, wherein the priming dose is 2500 µg.

5. The method of claim 3, wherein the priming dose is administered between one and 5 times before administering the second composition.

6. The method of claim 1, wherein the boosting dose is between 1 µg and 100 µg.

7. The method of claim 6, wherein the boosting dose is 50 µg.

8. The method of claim 6, wherein the boosting dose is 25 µg.

9. The method of claim 1, wherein the priming composition is administered by a method selected from IM, IV, ID, subcutaneously, mucosally, recombinant bacteria, recombinant virus, or gene gun, or combinations thereof.

10. The method of claim 1, wherein the boosting composition is administered by a method selected from IM, IV, ID, subcutaneously, mucosally, recombinant bacteria, recombinant virus, or gene gun, or combinations thereof.

11. The method of claim 1, wherein the CD8+ T cells comprise cytotoxic T lymphocytes.

12. The method of claim 1, wherein the priming composition comprises PfCSP.

13. The method of claim 1, wherein the boosting composition comprises RTS,S.

14. The method of claim 1, wherein the priming composition comprises substantially all of the circumsporozoite protein and the boosting composition comprises RTS,S.

15. The method of claim 1, wherein the malaria-causing pathogen is *P. falciparum*.

16. The method of claim 1, wherein the boosting composition comprises a hybrid protein comprising at least 160 amino acids of the C-terminal portion of the CS protein, four or more tandem repeats, each repeat consisting of the amino acids Asn-Ala-Asn-Pro (SEQ ID NO: 34), and the surface antigen from hepatitis B virus (HbsAg).

17. The method of claim 1, wherein the boosting composition comprises RTS,S and a Th1 inducing adjuvant.

* * * * *

SEQUENCE LISTING

```
<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Leu Asn Lys Ile Gln Asn Ser Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Pro Ser Asp Lys His Ile Lys Glu Tyr
```

-continued

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Thr Cys Gly Asn Gly Ile Gln Val Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Pro Lys Asp Glu Leu Asp Tyr
1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Lys Glu Tyr Leu Asn Lys Ile Gln Asn Ser Leu Ser Thr Glu Trp
1               5                   10                  15

Ser Pro Cys Ser
            20

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Tyr Leu Asn Lys Ile Gln Asn Ser Leu Ser Thr Glu Trp
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ile Glu Lys Lys Ile Cys Lys Met Glu Lys Cys Ser Ser Val Phe
1               5                   10                  15

Asn Val Val Asn Ser
            20

<210> SEQ ID NO 8
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Lys Pro Gly Ser Ala Asn Lys Pro Lys Asp Glu Leu Asp Tyr Ala
1               5                   10                  15

Asn Asp Ile Glu
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Glu Glu Pro Ser Asp Lys His Ile Lys Glu Tyr Leu Asn Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Lys His Ile Lys Glu Tyr Leu Asn Lys Ile Gln Asn Ser Leu
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Tyr Leu Asn Lys Ile Gln Asn Ser Leu Ser Thr Glu Trp Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Gln Asn Ser Leu Ser Thr Glu Trp Ser Pro Cys Ser Val Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 13

Ser Thr Glu Trp Ser Pro Cys Ser Val Thr Cys Gly Asn Gly Ile
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Cys Ser Val Thr Cys Gly Asn Gly Ile Gln Val Arg Ile Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Gly Asn Gly Ile Gln Val Arg Ile Lys Pro Gly Ser Ala Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Val Arg Ile Lys Pro Gly Ser Ala Asn Lys Pro Lys Asp Glu
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Gly Ser Ala Asn Lys Pro Lys Asp Glu Leu Asp Tyr Glu Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Pro Lys Asp Glu Leu Asp Tyr Glu Asn Asp Ile Glu Lys Lys
1               5                   10                  15

<210> SEQ ID NO 19
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Leu Asp Tyr Ala Asn Asp Ile Glu Lys Lys Ile Cys Lys Met Glu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Ile Glu Lys Lys Ile Cys Lys Met Glu Lys Cys Ser Ser Val Phe
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Cys Lys Met Glu Lys Cys Ser Ser Val Phe Asn Val Val Asn
1               5                   10                  15

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ile Leu Gly Phe Val Phe Thr Leu
1               5

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Asn Asn Phe Thr Val Ser Phe Trp Leu Arg Val Pro Lys Val Ser
1               5                   10                  15

Ala Ser His Leu Glu Thr
            20

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Leu Tyr Asn Thr Val Ala Thr Leu
```

```
<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gly Leu Leu Gly Asn Val Ser Thr Val Leu Leu Gly Gly Val
1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Tyr Leu Asn Lys Ile Gln Asn Ser Leu Ser Thr Glu Trp Ser
1               5                  10                  15

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ile Leu Gly Phe Val Phe Thr Leu
1               5

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttggtgatga tttgaacatt gga                                             23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cccagttcct gcagagtaga aaa                                             23

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
```

```
gaaggtgaag gtcggagtc                                                    19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaagatggtg atgggatttc                                                   20

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgtcacttgc aaacacacag cttgtcgaa                                         29

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caagcttccc gttctcagcc                                                   20

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Ala Asn Pro
1
```